United States Patent
Tuli

(10) Patent No.: US 11,911,470 B2
(45) Date of Patent: Feb. 27, 2024

(54) METHODS FOR TREATING PANCREATIC CANCER

(71) Applicant: Cedars-Sinai Medical Center, Los Angeles, CA (US)

(72) Inventor: Richard Tuli, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1162 days.

(21) Appl. No.: 16/530,380

(22) Filed: Aug. 2, 2019

(65) Prior Publication Data

US 2020/0114004 A1 Apr. 16, 2020

Related U.S. Application Data

(60) Provisional application No. 62/714,305, filed on Aug. 3, 2018.

(51) Int. Cl.
*A61K 41/00* (2020.01)
*A61N 5/10* (2006.01)
*C07K 16/28* (2006.01)

(52) U.S. Cl.
CPC ........ *A61K 41/0038* (2013.01); *A61N 5/1031* (2013.01); *A61N 5/1078* (2013.01); *C07K 16/2827* (2013.01); *A61N 2005/1098* (2013.01)

(58) Field of Classification Search
CPC .. A61K 31/4462; A61K 9/0019; A61K 31/05; A61K 31/165; A61K 31/17; A61K 31/175; A61K 31/19; A61K 31/341; A61K 31/495; A61P 17/06; A61P 17/04
See application file for complete search history.

(56) References Cited

PUBLICATIONS

Koo et al. (Radiat Oncol J 2016;34(4):250-259 ) (Year: 2016).*
Gong et al. Journal for Immuno Therapy of Cancer vol. 6, Article No. 46 (2018) (Year: 2018).*
Joshi et al. Journal of Clinical Oncology 36, No. 6_suppl (Feb. 20, 2018) 455-455 (Year: 2018).*
Feng et al. PD-1/PD-L1 and immunotherapy for pancreatic cancer Cancer Letters vol. 407, Oct. 28, 2017, pp. 57-65 (Year: 2017).*
Common Terminology Criteria for Adverse Events (CTCAE), U.S. Department of Health and Human Services, National Institutes of Health, National Cancer Institute, 2009, Version 4.03, pp. 1-78.
Guidance for Industry Drug-Induced Liver Injury: Premarketing Clinical Evaluation, U.S. Department of Health and Human Services, Food and Drug Administration, Center for Drug Evaluation and Research (CDER), Center for Biologics Evaluation and Research (CBER), 2009, pp. 1-25.
Gerber et al., IFN-γ Mediates the Antitumor Effects of Radiation Therapy in a Murine Colon Tumor, The American Journal of Pathology, 2013, vol. 182(6), pp. 2345-2354.
Narwal et al., Population Pharmacokinetics of Sifalimumab, an Investigational Anti-Interferon-α Monoclonal Antibody, in Systematic Lupus Erythematosus, Clin. Pharmacokinet, 2013, vol. 52, pp. 1017-1027.
Ng et al., Rationale for Fixed Dosing of Pertuzumab in Cancer Patients Based on Population Pharmacokinetic Analysis, Pharmaceutical Research, 2006, vol. 23(6), pp. 1275-1284.
Stone et al., Effect of Host Immune Capability on Radiocurability and Subsequent Transplantability of a Murine Fibrosarcoma, JNCI, 1979, vol. 63(5), pp. 1229-1235.
Verbrugge et al., Radiotherapy Increases the Permissiveness of Established Mammary Tumors to Rejection by Immunomodulatory Antibodies, American Association for Cancer Research, 2012, vol. 72(13), pp. 3163-3174.
Wang et al., Population Pharmacokinetic and Pharmacodynamic Analysis of Tremelimumab in Patients With Metastatic Melanoma, The Journal of Clinical Pharmacology, 2014, vol. 54(10), pp. 1108-1116.
Wang et al., Fixed Dosing Versus Body Size-Based Dosing of Monoclonal Antibodies in Adult Clinical Trials, Pharmacokinetics and Pharmacodynamics, Journal of Clinical Pharmacology, 2009, vol. 49, pp. 1012-1024.
Zeng et al., Anti-PD-1 Blockade and Stereotactic Radiation Produce Long-Term Survival in Mice With Intracranial Gliomas, Int J Radiat Oncol Biol Phys., 2013, vol. 86(2), pp. 343-349.
Zhang et al., Fixed Dosing Versus Body Size-Based Dosing of Therapeutic Peptides and Proteins in Adults, Pharmacokinetics and Pharmacodynamics, Journal of Clinical Pharmacology, 2012, vol. 52, pp. 18-28.

* cited by examiner

*Primary Examiner* — Jeffrey S Lundgren
*Assistant Examiner* — William Y Lee
(74) *Attorney, Agent, or Firm* — Nixon Peabody LLP; Linda B. Huber

(57) ABSTRACT

Provided herein are methods for treating pancreatic cancer using a combination of radiotherapy and an agent that inhibits binding of PD-L1 to PD1 (e.g., durvalumab).

22 Claims, 10 Drawing Sheets

9/1/17 - PreTx

10/25/17 – 4 wks post SBRT

METHODS FOR TREATING PANCREATIC CANCER

CROSS-REFERENCE TO RELATED APPLICATIONS

This application includes a claim of priority under 35 U.S.C. § 119(e) to U.S. provisional patent application No. 62/714,305 filed Aug. 3, 2018, the entirety of which is hereby incorporated by reference.

FIELD OF THE INVENTION

The invention relates to medicine, oncology, radiation, radiology, and nuclear medicine.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Pancreatic cancer is a devastating disease. Long term survival is only achievable in patients who undergo definitive resection. Unfortunately, only 10-15% of patients have tumors which are amenable to complete R0 resection due to arterial or venous vessel involvement. Indeed, numerous studies have shown suboptimal clinical outcomes in patients undergoing microscopically (R1) or macroscopically (R2) incomplete resections for pancreatic adenocarcinoma, thus leading to the clinical states of borderline-resectable and locally advanced unresectable pancreatic cancer; both defined by degree of vessel involvement and likelihood of downstaging with neoadjuvant chemotherapy and radiotherapy. Unfortunately, the vast majority of pancreatic tumors develop in the head and neck in close proximity to the superior mesenteric artery, celiac artery, or splenoportal confluence resulting in approximately 40% of newly diagnosed patients with BL or LA PC. Current treatment of these patients results in dismal median survival rates of 11-12 months, poor local control and downstaging rates of only 10-15% with chemoradiotherapy. Gemcitabine has been used as a single agent, as well as in combination with other drugs, for the primary treatment of locally advanced and metastatic pancreatic carcinomas. Response rates of 11-22% have been reported in heavily pre-treated patients, and up to 42% in chemo naïve patients. Whereas its value has been substantiated in many clinical trials, its use with concurrent radiation therapy remains controversial with mixed results. A Phase I study evaluated radiation dose escalation using three-dimensional conformal techniques with full-dose gemcitabine, yet it was not possible to escalate the dose beyond 36 Gray (Gy; 2.4 Gy daily fractions) secondary to gastrointestinal toxicities. A follow-up multi-center Phase II study confirmed this regimen to be well-tolerated, while showing response rates of 5.1% and disease control rates of 84.6%. In an attempt to minimize dose-limiting toxicities to organs-at-risk and simultaneously allow an increase in target dose, outcomes (response rate of 52.4%, median overall survival 23.1 months) have been reported using dose-escalated intensity modulated radiation therapy (IMRT) with full-dose gemcitabine (Ben-Josef 2008 ASCO). Unfortunately, other contemporary trials have failed to show such promising results with the use of concurrent radiation therapy (Chauffert 2008; Loehrer 2008 ASCO).

Whereas the increased propensity for metastatic relative to local progression has tended to define treatment paradigms, recent data suggest that failure to control the primary tumor also results in complications that contribute to mortality in approximately 30% of patients. As a result, studies have attempted to intensify radiotherapy dosing not only to improve local control, but also downstaging rates with the hope of converting a significantly larger percentage of patients to technically resectable status, thereby allowing curative surgery. The design of such studies has paralleled technologic advances in radiation treatment delivery, such as intensity modulated radiotherapy and stereotactic body radiotherapy to allow dose escalation, as well as image-guidance modalities such as 4-dimensional CT/MRI and positron emission tomography (PET) to improve treatment accuracy and response evaluation. Early experience with SBRT has shown promising local control rates with still modest rates of downstaging. Koong et al. investigated the use of a 25 Gy single fraction alone or following 45 Gy of standard fractionated chemoradiation, resulting in excellent local control rates of 80-90% and acceptable toxicity, yet with downstaging rates similar to those seen with conventionally fractionated radiotherapy due to persistent tumor-vessel involvement. As a result, more effective multimodal treatment strategies are required and clinical trials integrating novel therapeutic agents should be initiated.

Durvalumab is a human monoclonal antibody (mAb) of the immunoglobulin G (IgG) 1 kappa subclass that inhibits binding of programmed death-ligand 1 (PD-L1) to its receptor programmed cell death protein 1 (PD-1) and CD80 and is being developed by AstraZeneca/MedImmune for use in the treatment of cancer. As durvalumab is an engineered mAb, it does not induce antibody-dependent cellular cytotoxicity or complement-dependent cytotoxicity. The mechanism of action for durvalumab is believed to be interference of the interaction of PD-L1 with PD-1 and CD80.

Provided herein are methods for treating pancreatic cancer using a combination of radiotherapy and an agent that inhibits binding of PD-L1 to PD1 (e.g., durvalumab).

SUMMARY OF THE INVENTION

Various embodiments of the present invention provide a method of treating a cancer in a subject, comprising: administering to the subject an effective amount of an agent that inhibits binding of PD-L1 to PD1; and administering to the subject an effective dose of radiotherapy, thereby treating the cancer in the subject. In some embodiments, the agent is durvalumab. In some embodiments, the radiotherapy is focused radiotherapy, external beam radiation therapy, conventional external beam radiation therapy (2DXRT), image guided radiotherapy (IGRT), three-dimensional conformal radiation therapy (3D-CRT), intensity modulated radiation therapy (IMRT), helical tomotherapy, volumetric modulated arc therapy (VMAT), particle therapy, proton beam therapy, conformal proton beam radiation therapy, auger therapy (AT), stereotactic radiation therapy, stereotactic radiosurgery (SRS), stereotactic body radiation therapy (SBRT), brachytherapy, internal radiation therapy, intraoperative radiation therapy (IORT), radioimmunotherapy, radioisotope therapy, hyperfractionated radiotherapy, or hypofractionated radiotherapy, or a combination thereof. In some embodiments, the inhibitor and the radiotherapy are administered sequentially. In some embodiments, the inhibitor and the radiotherapy are administered simultaneously. In some embodiments, the subject is a human. In some embodiments, the cancer is pancreatic cancer. In some embodiments, the subject has borderline resectable and locally advanced unresectable pancreatic ductal adenocarcinoma (PDA). In some embodiments, the agent is durvalumab and is administered in the amount of about 100 mg-1000 mg, 100 mg-900 mg, 100 mg-800 mg, 100 mg-700 mg, 100 mg-600 mg, 100 mg-500 mg, 100 mg-400 mg, 100 mg-300 mg, 100 mg-200 mg, 200 mg-800 mg, 300 mg-800 mg, 400 mg-800 mg, 500 mg-800 mg, 600 mg-800 mg, 700 mg-800 mg, 250 mg-500 mg, 250 mg-800 mg, 250 mg-1000 mg, 500 mg-1000 mg, 800 mg-1000 mg or combinations thereof. In some embodiments, the agent is durvalumab and is administered about every 1-21 days, 1-14 days, 1-10 days, 1-7 days, 1-5 days, 3-10 days, 5-10 days, 7-14 days, 7-21 days, 10-14 days, 10-21 days, 14-21 days or combinations thereof. In some embodiments, the agent is durvalumab and is administered for about 1-5 weeks, 5-7 weeks, 7-10 weeks, 10-12 weeks, or combinations thereof. In some embodiments, the radiotherapy is SABR and is administered at a dosage of about 5-7Gy per fraction delivered every alternate day for 5-7 fractions. In some embodiments, the radiotherapy is SABR and is administered at a dosage of about 6.6 Gy per fraction delivered every alternate day for 5 fractions.

Various embodiments of the present invention provide for a method of treating a cancer in a subject, comprising: administering to the subject an effective amount of an agent that inhibits binding of PD-L1 to PD1; and administering to the subject an effective dosage of radiotherapy, thereby treating the cancer in the subject.

In various embodiments, the agent can be durvalumab.

In various embodiments, the agent can be a PD1 inhibitor selected from the group consisting of pembrolizumab, nivolumab, pidilizumab, AMP-224, AMP-514, spartalizumab, cemiplimab, AK105, BCD-100, BI 754091, JS001, LZMO09, MGA012, Sym021, TSR-042, MGD013, AK104, XmAb20717, tislelizumab, PF-06801591, anti-PD1 antibody expressing pluripotent killer T lymphocytes (PIK-PD-1), autologous anti-EGFRvIII 4SCAR-IgT cells, and combinations thereof.

In various embodiments, the agent can be a PDL1 inhibitor selected from the group consisting of BGB-A333, CK-301, FAZ053, KN035, MDX-1105, MSB2311, SHR-1316, atezolizumab, avelumab, durvalumab, BMS-936559, CK-301, M7824, and combinations thereof.

In various embodiments, the radiotherapy can be focused radiotherapy, external beam radiation therapy, conventional external beam radiation therapy (2DXRT), image guided radiotherapy (IGRT), three-dimensional conformal radiation therapy (3D-CRT), intensity modulated radiation therapy (IMRT), helical tomotherapy, volumetric modulated arc therapy (VMAT), particle therapy, proton beam therapy, conformal proton beam radiation therapy, auger therapy (AT), stereotactic radiation therapy, stereotactic radiosurgery (SRS), stereotactic body radiation therapy (SBRT), brachytherapy, internal radiation therapy, intraoperative radiation therapy (IORT), radioimmunotherapy, radioisotope therapy, hyperfractionated radiotherapy, or hypofractionated radiotherapy, or a combination thereof.

In various embodiments, the subject can be human.

In various embodiments, the cancer can be pancreatic cancer.

In various embodiments, the subject can have borderline resectable and locally advanced unresectable pancreatic ductal adenocarcinoma (PDA).

In various embodiments, the agent can be durvalumab and can be administered in the amount of about 100 mg-1000 mg, 100 mg-900 mg, 100 mg-800 mg, 100 mg-700 mg, 100 mg-600 mg, 100 mg-500 mg, 100 mg-400 mg, 100 mg-300 mg, 100 mg-200 mg, 200 mg-800 mg, 300 mg-800 mg, 400 mg-800 mg, 500 mg-800 mg, 600 mg-800 mg, 700 mg-800 mg, 250 mg-500 mg, 250 mg-800 mg, 250 mg-1000 mg, 500 mg-1000 mg, 800 mg-1000 mg or combinations thereof.

In various embodiments, the agent can be durvalumab and can be administered in an amount of about 750 mg. In various embodiments, the agent can be durvalumab and can be administered about every 1-5 weeks. In various embodiments, the agent can be durvalumab and can be administered about every 14 days. In various embodiments, the agent can be durvalumab and can be administered about every 28 days. In various embodiments, the agent can be durvalumab and can be administered for about 2-50 weeks. In various embodiments, the agent can be durvalumab and can be administered for about 10-50 weeks.

In various embodiments, the radiotherapy can be stereotactic body radiation therapy (SBRT) and can be administered at a dosage of about 5-7Gy per fraction delivered about every alternate day for 5-7 fractions. In various embodiments, the radiotherapy can be stereotactic body radiation therapy (SBRT) and can be administered at a dosage of about 6.6 Gy per fraction delivered about every alternate day for 5 fractions.

In various embodiments, the agent can be administered about every 14 days or about every 28 days, and the radiotherapy can be administered starting on about day 8, calculated from the first day of administering the agent.

Various embodiments provide for a method of treating borderline resectable or locally advanced pancreatic adenocarcinoma in a subject, comprising: administering to the subject about 750 mg of durvalumab about every 14 days or about every 28 days; and administering to the subject stereotactic ablative body radiotherapy (SABR) starting on about day 8, calculated from the first day of administering durvalumab, at about 6.6 Gy per fraction about every other day for 5 fractions, thereby treating the borderline resectable or locally advanced pancreatic adenocarcinoma in the subject.

In various embodiments, the durvalumab is administered until surgical resection.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
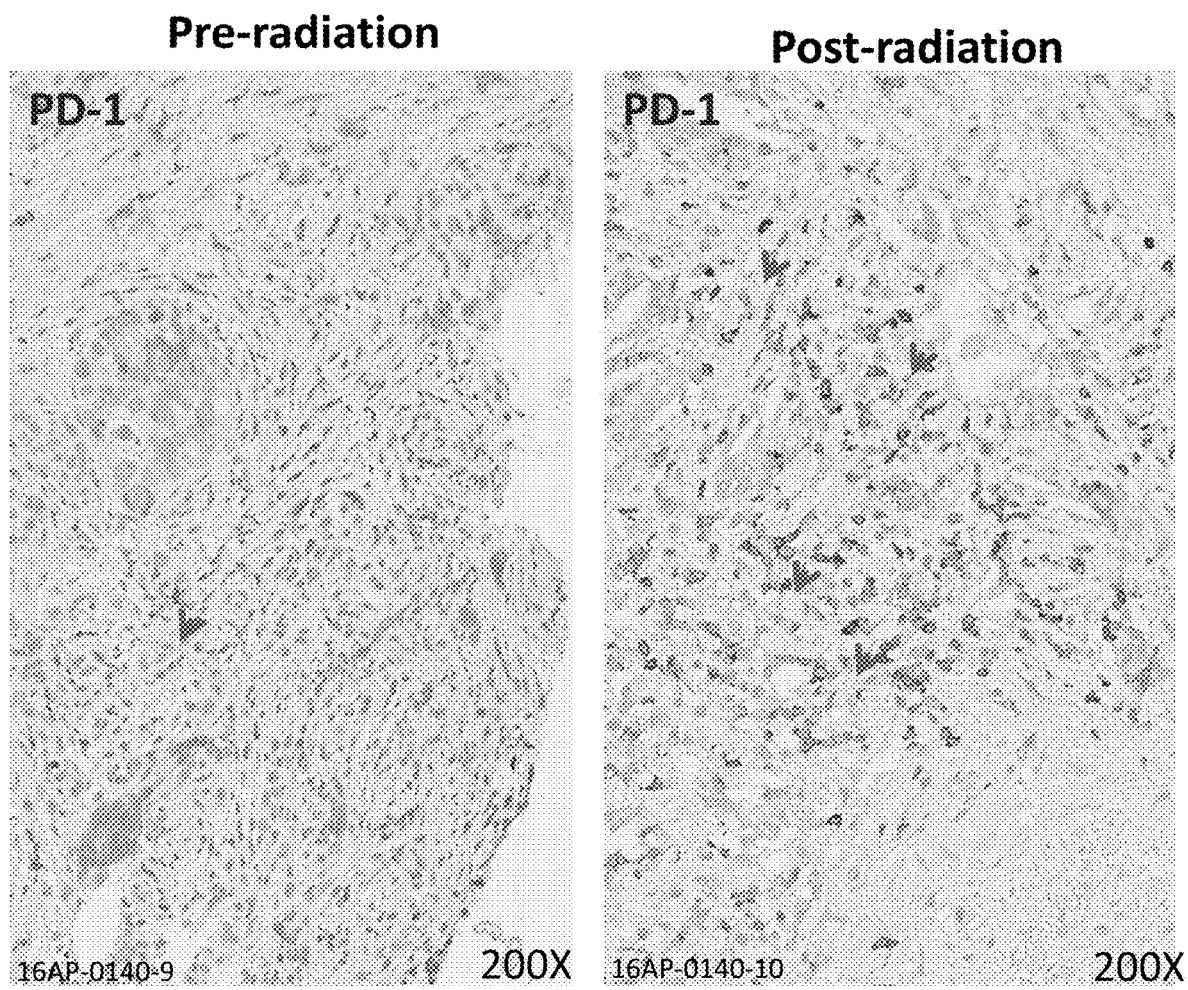
FIG. 1 depicts a representative example of the effect of radiotherapy on the expression of pancreatic intratumoral PD-1 expression. Before radiation (left panel), protein expression is sparse, whereas there is significant upregulation of PD-1 protein 6 weeks post radiation providing a potential therapeutic target for anti-PD-1 therapy.
Figure 2:
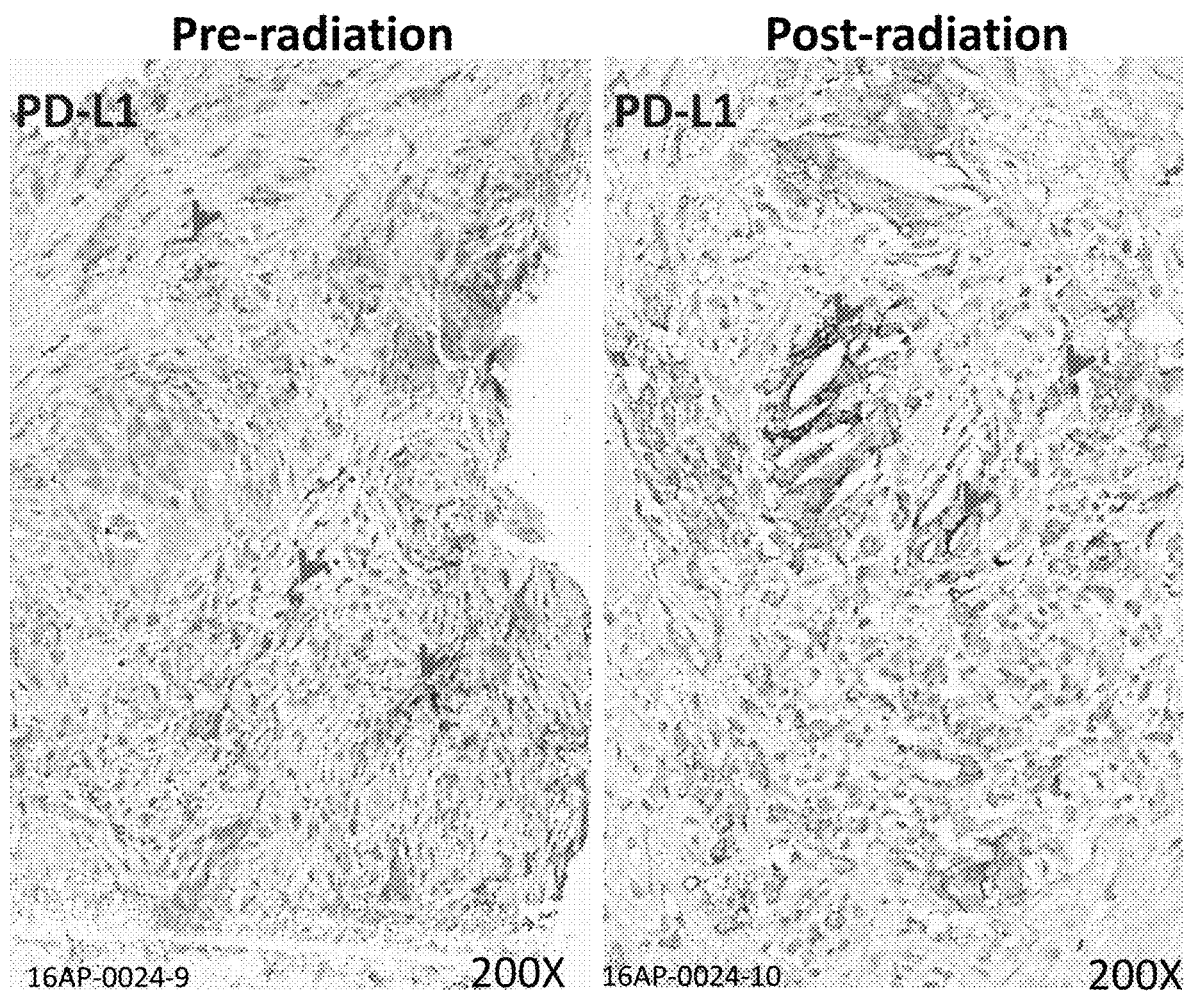
FIG. 2 depicts another representative example of the effect of radiotherapy on the expression of pancreatic intratumoral PD-L1 expression. Before radiation (left panel), protein expression is sparse, whereas there is significant upregulation of PD-L1 protein 6 weeks post radiation providing a potential therapeutic target for anti-PD-1 therapy.
Figure 3:
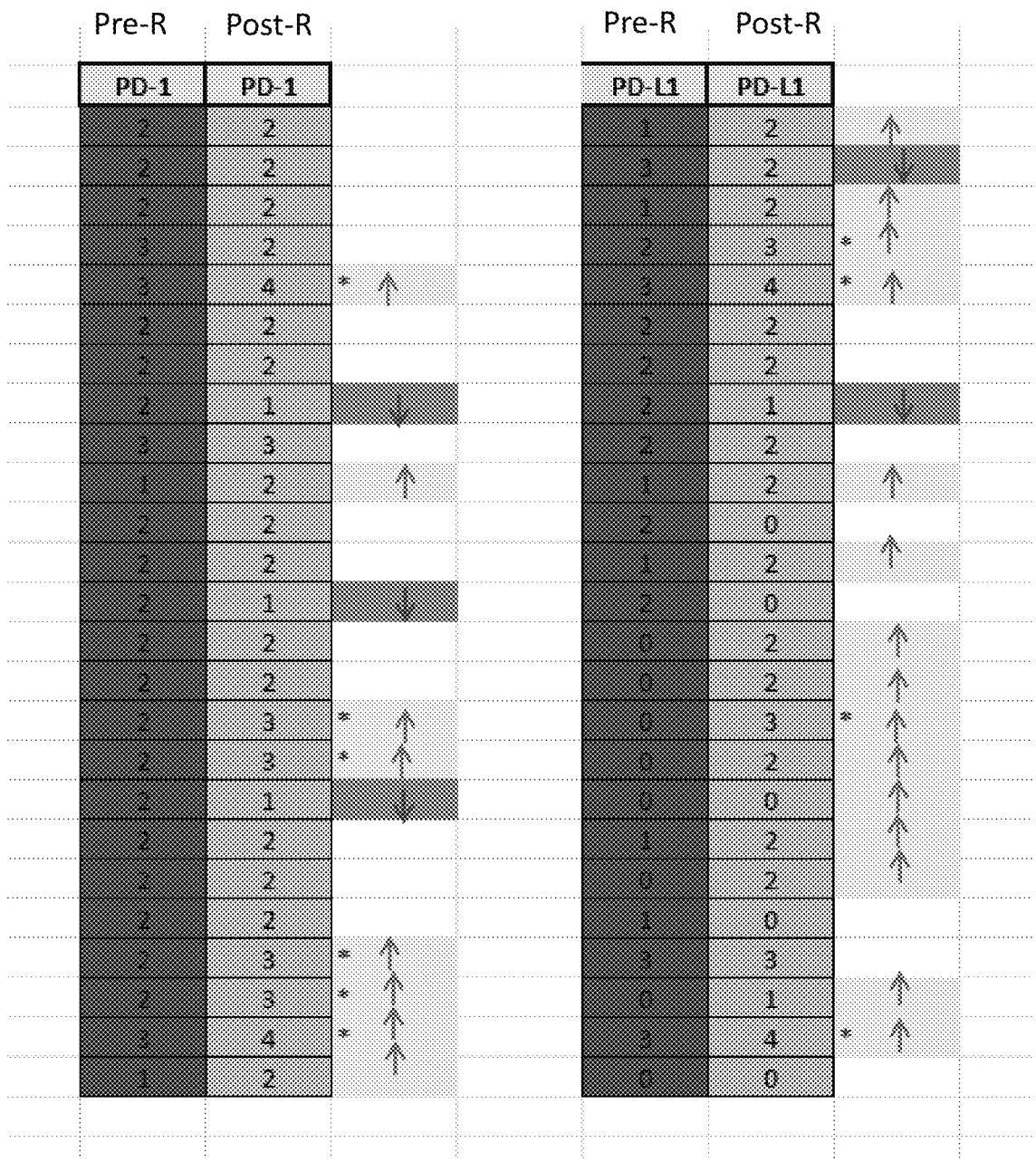
FIG. 3 depicts immunohistochemical quantitation of PD-1 and PD-L1 before and after radiation in 25 patients treated with chemoradiation shows significant upregulation of both proteins in the majority of patients suggesting both immunologic checkpoints as targets of durvalumab.
Figure 4A:
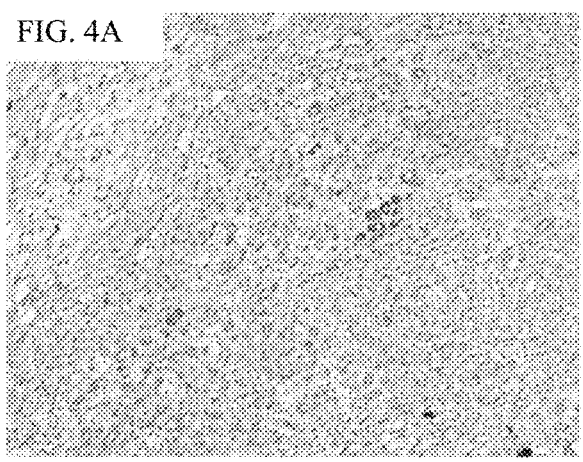
FIG. 4A-4C depict PD-L 1 staining of pre-radiotherapy treatment naive (A) and post-radiotherapy (B) pancreatic adenocarcinoma specimens show quantitative up-regulation of expression in percentage of PD-L1 cells. Serum cytokine expression following RT shows marked inflammation with IFN-gamma production.
Figure 4B:
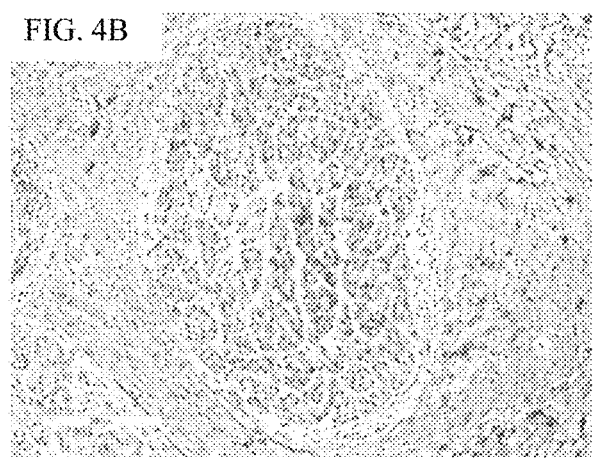
Figure 4C:
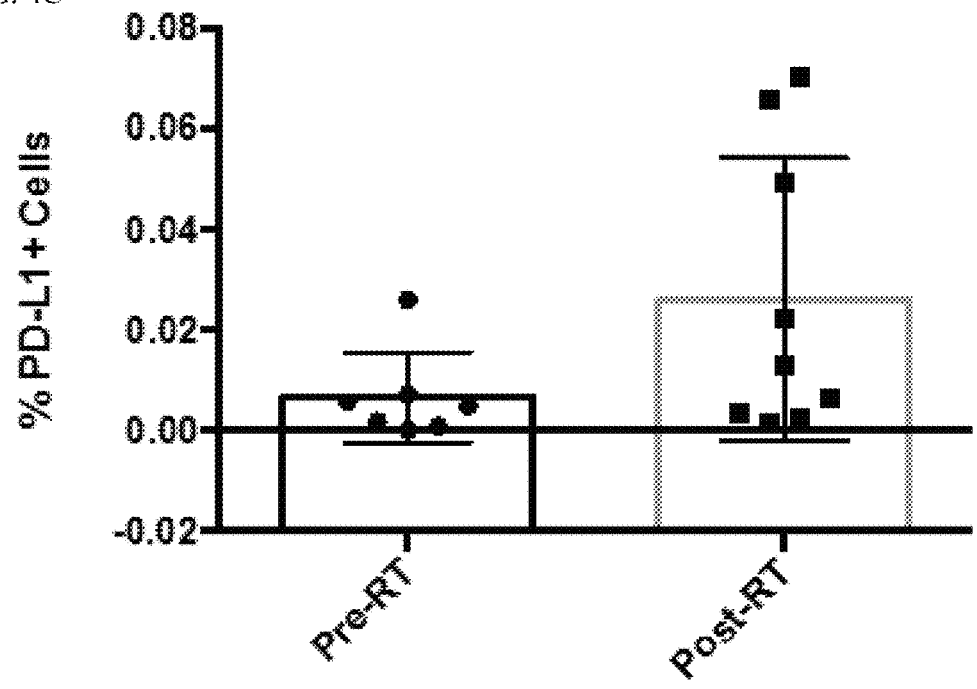
Figure 5A:
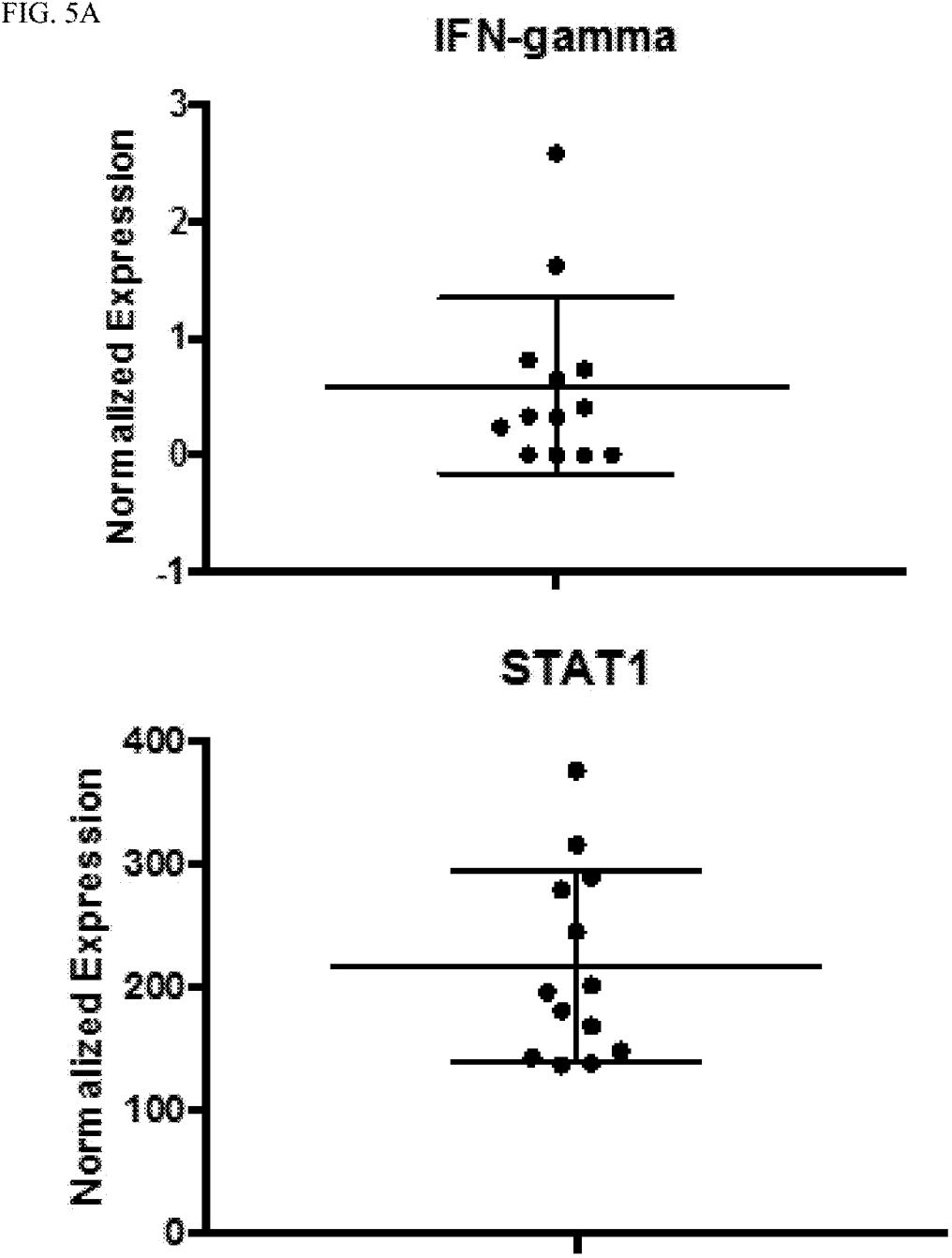
FIGS. 5A-5B show that pancreatic cancer biopsies show baseline levels of PD-L1 and PD-L2 expression. Biopsy samples from pancreatic tumors prior to treatment were analyzed using RNASeq. While IFN-gamma levels at baseline are low in tumors (FIG. 5A, upper panel), there is substantial STAT1 expression (FIG. A, lower panel) suggesting the potential for a rapid response to IFN-gamma leading to potential upregulation of PD-L1/2. Additionally, there is little PD-1 expression in tumors at baseline (FIG. 5B, upper panel), but there is expression of PD-L1 and PD-L2 in all tumors (FIG. 5B, lower panels) highlighting the possibility that pancreatic tumors evade the immune system using PD-L1 mediated immunosuppression.
Figure 5B:
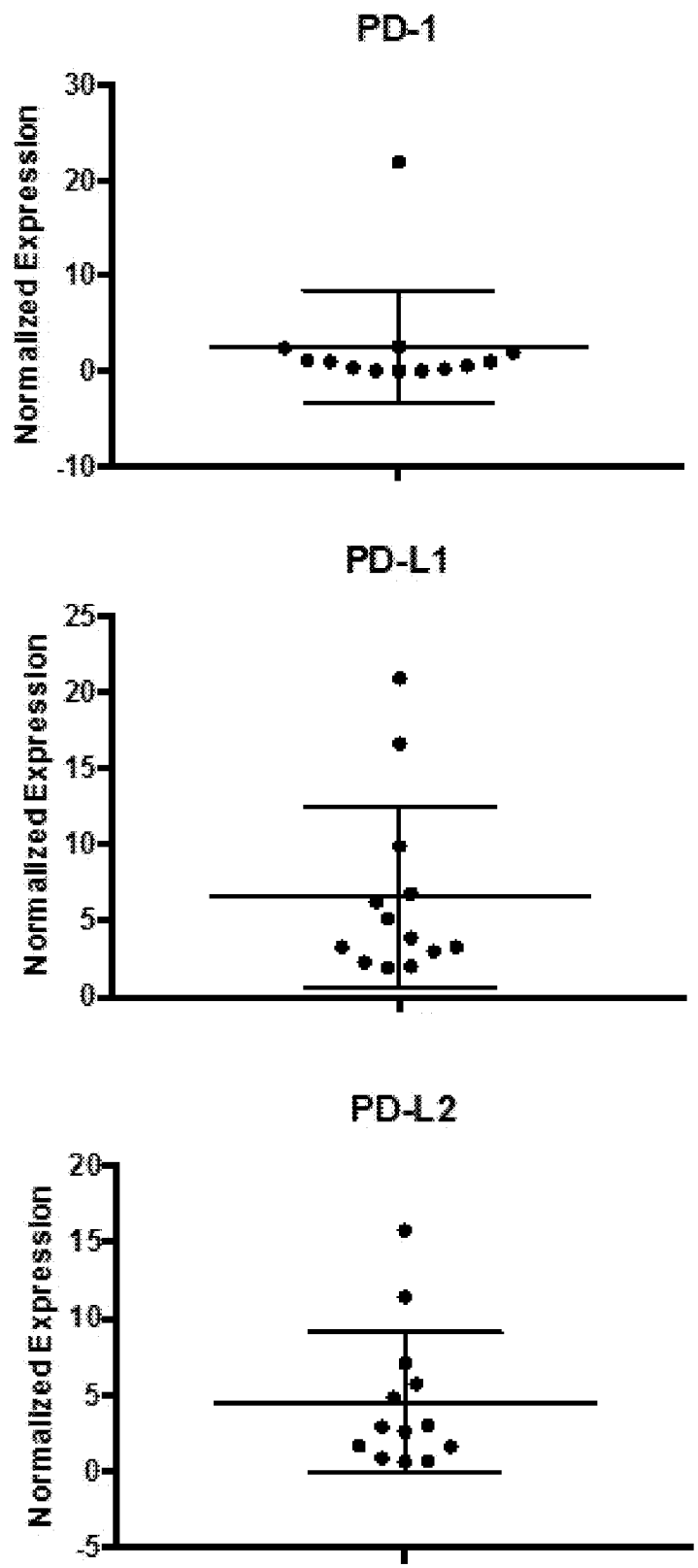
Figure 6:
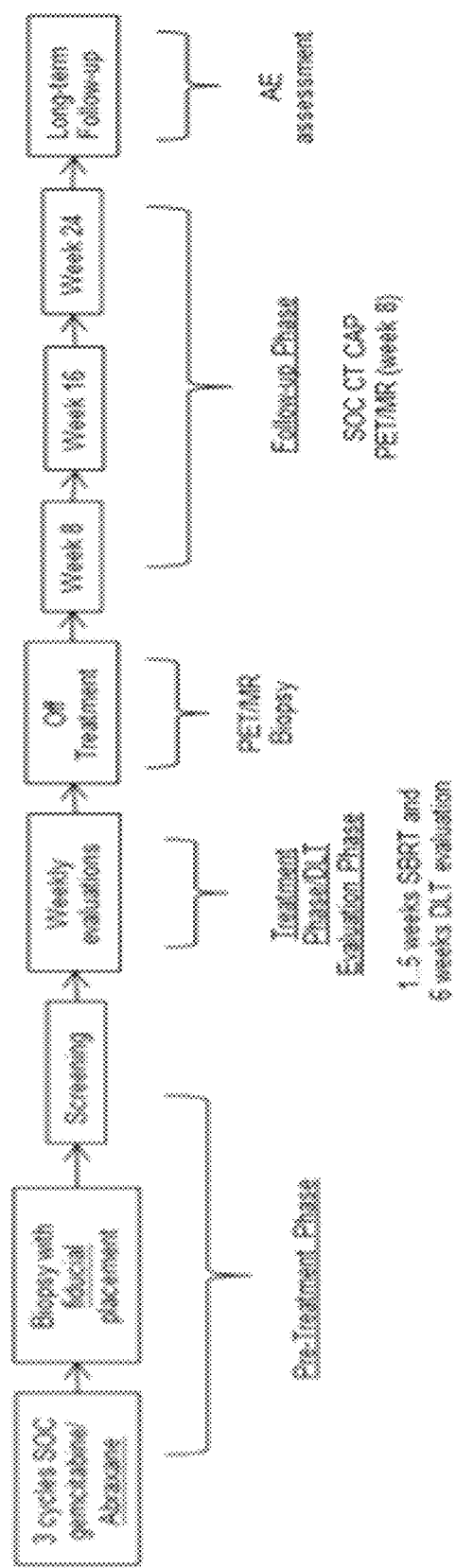
FIG. 6 depicts a study schema of a Phase I/II Study of Durvalumab (PDL1-I), SBRT in BR/LAPC.
Figure 7:
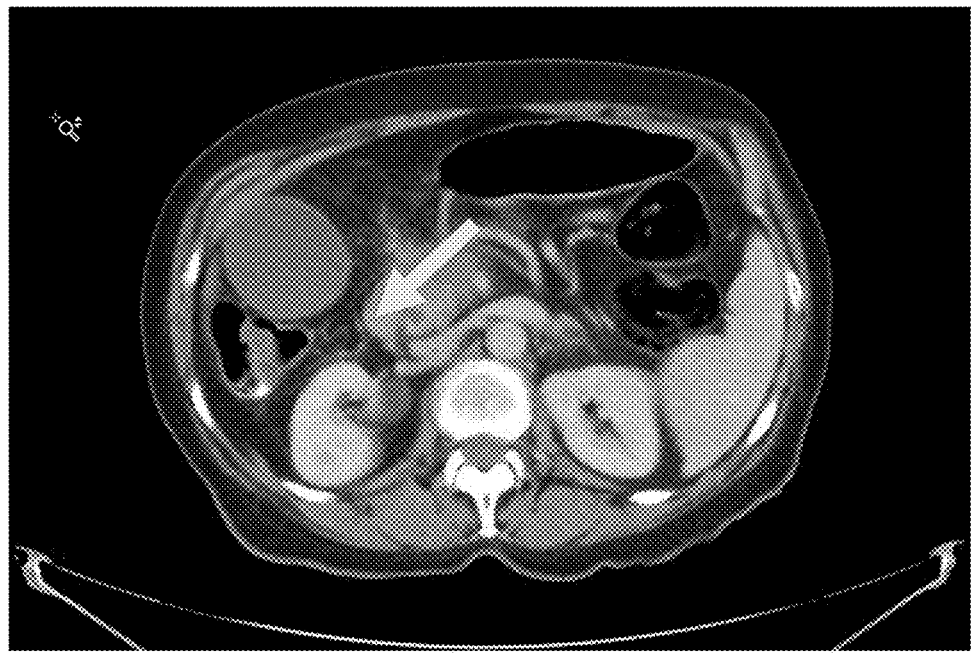
FIG. 7 depicts an axial CT scan of subject #1 enrolled in phase ½ clinical trial of SBRT with durvalumab pre (left) and 6 weeks post (right) completion of SBRT shows significant partial response of locally advanced pancreatic tumor (yellow arrow) with reduction in size and improved patency of involved blood vessels.
Figure 7:
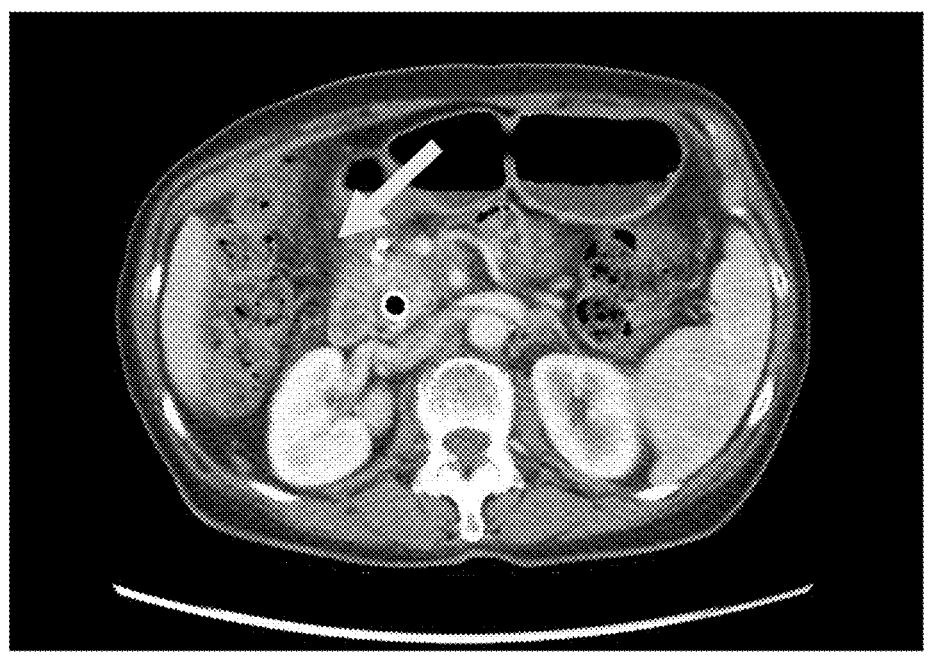
Figure 8A:
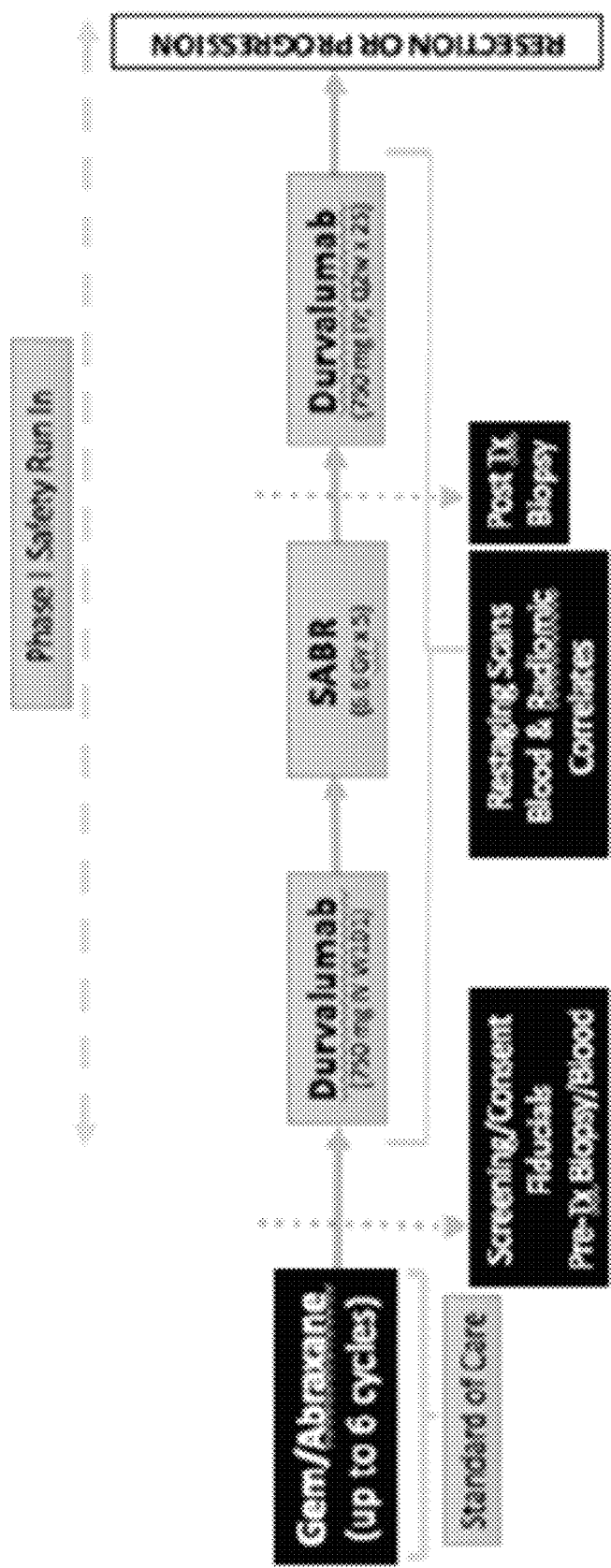
FIGS. 8A-8B depict another study schema of a Phase I/II Study of Durvalumab, SBRT.
Figure 8B:
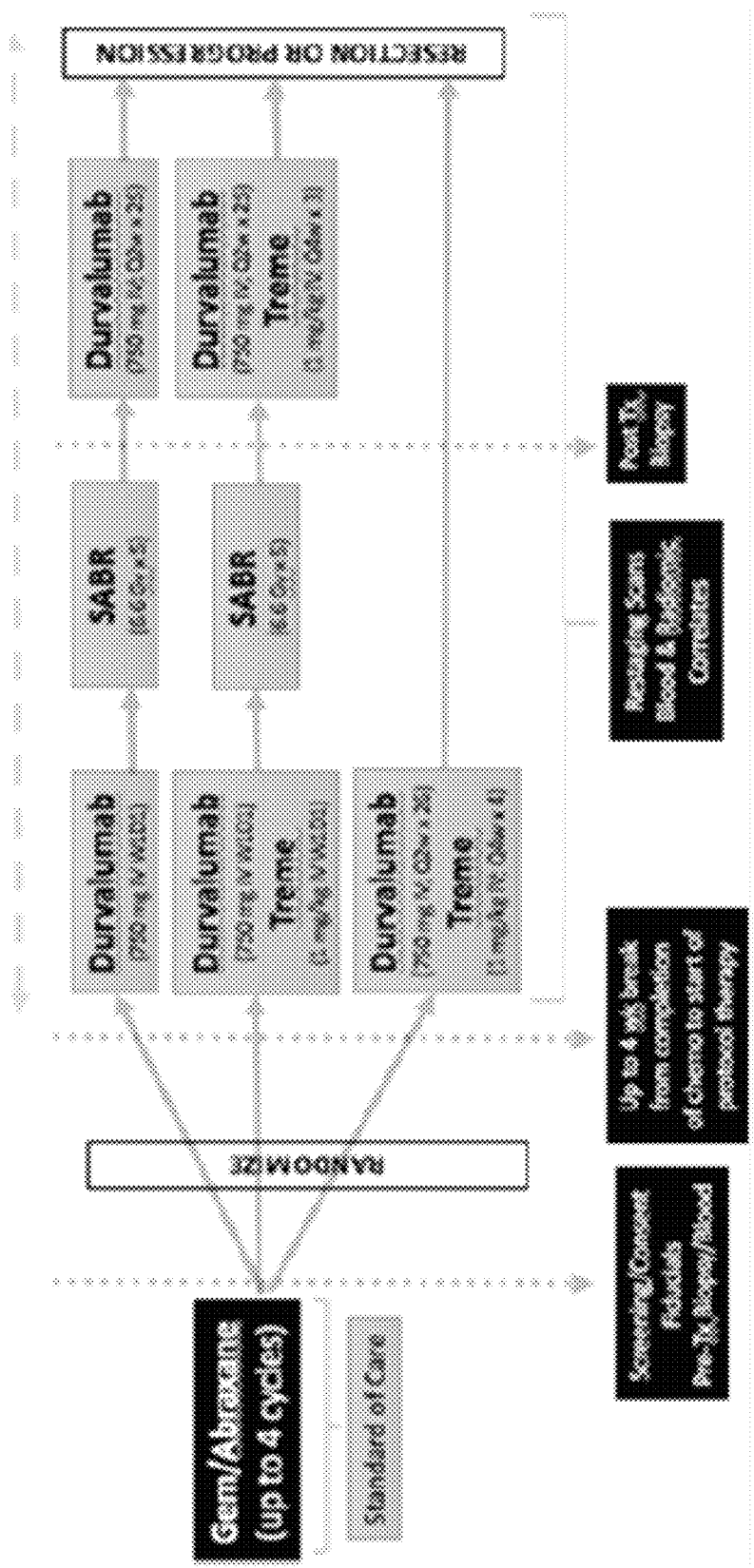

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22$^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3$^{rd}$ ed., revised ed., J. Wiley & Sons (New York, NY 2006); Smith, March's Advanced Organic Chemistry Reactions, Mechanisms and Structure 7$^{th}$ ed., J. Wiley & Sons (New York, NY 2013); Singleton, Dictionary of DNA and Genome Technology 3$^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "about" when used in connection with a referenced numeric indication means the referenced numeric indication plus or minus up to 10% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 5%, 4%, 3%, 2% or 1% of that referenced numeric indication, if specifically provided for in the claims.

As used herein the term "about" when used in connection with a referenced number of days less than 1 week, means the number of days plus or minus ½ day; when used in connection with a referenced number of weeks that are less than 4 weeks, means the number of weeks plus or minus 4 days (or if specifically provided in the claims, means the number of weeks plus or minus 1, 2, or 3 days); when used in connection with a referenced number of months that are less than 1 year, means the number of months plus or minus 1 month (or if specifically provided for in the claims, means the number of months plus or minus 1, 2, 3 or 4 weeks); when used in connection with a referenced number of years less than 10 years, means the number of years plus or minus 1 year (or if specifically provided for in the claims, means the number of years plus or minus 1, 2, 3, 4, 5, 6, 7, 8, 9, 10, 11, or 12 months).

As used herein the term "about" when used in connected with the phrase "every alternate day" or "every other day" with respect to radiation treatment, can allow for having 2 days in between radiation dosages. For example, in a treatment week, for convenience, a subject may be treated on a Friday, and then treated on a Monday, and continue the "every alternate day" treatment. As another example, the subject, for convenience, may occasionally have two days in between the radiation dosages.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to therapeutic treatment, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of pancreatic cancer, delay or slowing of pancreatic cancer, and amelioration or palliation of symptoms associated with pancreatic cancer.

The term "effective amount" as used herein with respect to an agent that inhibits binding of PD-L1 to PD1 (e.g., durvalumab) and/or radiotherapy as disclosed herein, refers to the amount of to decrease at least one or more symptom of the disease or disorder, and relates to a sufficient amount of agent and/or radiotherapy to provide the desired effect. The phrase "therapeutically effective amount" as used herein means a sufficient amount of the agent and/or radiotherapy to treat a disorder, at a reasonable benefit/risk ratio applicable to any medical treatment.

A therapeutically or prophylactically significant reduction in a symptom is, e.g. at least 10%, at least 20%, at least 30%, at least 40%, at least 50%, at least 60%, at least 70%, at least 80%, at least 90%, at least 100%, at least 125%, at least 150% or more in a measured parameter as compared to a control or non-treated subject or the state of the subject prior to administering the agent and/or radiotherapy as described herein. Measured or measurable parameters include clinically detectable markers of disease, for example, elevated or depressed levels of a biological marker, as well as parameters related to a clinically accepted scale of symptoms or markers for cancer (e.g., pancreatic cancer). It will be understood, however, that the total daily usage of the compositions (e.g., agent that inhibits binding of PD-L1 to PD1 (e.g., durvalumab)) and formulations as disclosed herein will be decided by the attending physician within the scope of sound medical judgment. The exact amount required will vary depending on factors such as the type of disease being treated, gender, age, and weight of the subject.

"Diseases", "conditions" and "disease conditions," as used herein may include, but are in no way limited to any form of malignant neoplastic cell proliferative disorders or diseases. Examples of such disorders include but are not limited to cancer and tumor.

A "cancer" or "tumor" as used herein refers to an uncontrolled growth of cells which interferes with the normal functioning of the bodily organs and systems, and/or all neoplastic cell growth and proliferation, whether malignant or benign (unless specifically indicated as a benign tumor), and all pre-cancerous and cancerous cells and tissues. A subject that has a cancer or a tumor is a subject having objectively measurable cancer cells present in the subject's body. Included in this definition are benign and malignant tumors, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue. Melanoma is an invasive form of skin tumor. As used herein, the term "carcinoma" refers to a cancer arising from epithelial cells. Examples of cancer include, but are not limited to, nervous system tumor, brain tumor, nerve sheath tumor, breast cancer, colorectal cancer, colon cancer, rectal cancer, bowel cancer, carcinoma, lung cancer, hepatocellular cancer, gastric cancer, pancreatic cancer, cervical cancer, ovarian cancer, liver cancer, bladder cancer, cancer of the urinary tract, thyroid cancer, renal cancer, renal cell carcinoma, carcinoma, melanoma, head and neck cancer, brain cancer, and prostate cancer, including but not limited to androgen-dependent prostate cancer and androgen-independent prostate cancer. Examples of brain tumor include, but are not limited to, benign brain tumor, malignant brain tumor, primary brain tumor, secondary brain tumor, metastatic brain tumor, glioma, glioblastoma, glioblastoma multiforme (GBM), medulloblastoma, ependymoma, astrocytoma, pilocytic astrocytoma, oligodendroglioma, brainstem glioma, optic nerve glioma, mixed glioma such as oligoastrocytoma, low-grade glioma, high-grade glioma, supratentorial glioma, infratentorial glioma, pontine glioma, meningioma, pituitary adenoma, and nerve sheath tumor. Nervous system tumor or nervous system neoplasm refers to any tumor affecting the nervous system. A nervous system tumor can be a tumor in the central nervous system (CNS), in the peripheral nervous system (PNS), or in both CNS and PNS. Examples of nervous system tumor include but are not limited to brain tumor, nerve sheath tumor, and optic nerve glioma.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A "subject" can be one who has been previously diagnosed with or identified as suffering from or having a condition in need of treatment (e.g., pancreatic cancer) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

The term "sample" or "biological sample" as used herein denotes a sample taken or isolated from a biological organism, e.g., a fluid sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; tissue sample; tumor sample; and/or tumor biopsy etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

In accordance with the present invention, the term "radiation therapy" or "radiotherapy" refers to a cancer treatment that uses high-energy particles or waves, such as x-rays, gamma rays, electron beams, or protons, to destroy or damage cancer cells or prevent them from growing and dividing. Other names for radiation therapy include irradiation or x-ray therapy. Radiation can be given alone or used with other treatments, such as surgery or chemotherapy. In fact, certain drugs are known to be radiosensitizers. This means they can actually make the cancer cells more sensitive to radiation, which helps the radiation to better kill cancer cells. Depending on the cancer type and location, there are also three different ways to give radiation therapy: external radiation, internal radiation, and systemic radiation. Sometimes a patient gets more than one type of radiation therapy for the same cancer.

External radiation (or external beam radiation) therapy uses a machine that directs high-energy rays from outside the body into the tumor. External radiation therapy is usually given with a machine called a linear accelerator (often called a "linac" for short). Types of external radiation therapy include but are not limited to standard external beam radiation therapy, conventional external beam radiation therapy (2DXRT), image guided radiotherapy (IGRT), three-dimensional conformal radiation therapy (3D-CRT), intensity modulated radiation therapy (IMRT), helical tomotherapy, volumetric modulated arc therapy (VMAT), particle therapy, proton beam therapy, carbon ion therapy, conformal proton beam radiation therapy, auger therapy (AT), intraoperative radiation therapy (IORT), stereotactic radiation therapy, stereotactic radiosurgery (SRS), and stereotactic ablative radiotherapy (SABR) also known as stereotactic body radiation therapy (SBRT). There are three different ways of giving SRS: the most common type uses a movable linac that's controlled by a computer to move around to target the tumor from many different angles (e.g., X-KNIFE, CYBERKNIFE, and CLINAC); the second type is the GAMMA KNIFE, which uses about 200 small beams aimed at the tumor from different angles for a short period of time to deliver a large dose of radiation; and the third type uses heavy charged particle beams (like protons or helium ion beams) to deliver radiation to the tumor.

Internal radiation therapy (also called brachytherapy) uses a radioactive source that's put inside the body in or near the tumor. The main types of brachytherapy are intracavitary radiation and interstitial radiation. Both of these methods use radioactive implants such as pellets, seeds, ribbons, wires, needles, capsules, balloons, or tubes. High-dose-rate (HDR) brachytherapy allows a person to be treated for only a few minutes at a time with a powerful radioactive source that's put in the applicator, and the source is removed after several minutes. Low-dose-rate brachytherapy uses the implant to give off lower doses of radiation over a longer period of time.

Systemic radiation therapy uses radioactive drugs (called radiopharmaceuticals) to treat certain types of cancer. These drugs can be given by mouth or put into a vein; they then travel throughout the body. These radiation sources are in the form of a liquid made up of a radioactive substance, and they are sometimes attached with a targeting agent that guides them to cancers and tumors. For example, a monoclonal antibody can be used to target the radioactive substance to the cancer cells, that is, a radioimmunotherapy. Radioimmunotherapy is a type of systemic radiation therapy, in which monoclonal antibodies are attached to the radioactive substance. Monoclonal antibodies are laboratory-made proteins designed to recognize specific factors only found in cancer cells, and they can deliver low doses of radiation directly to the tumor while leaving noncancerous cells alone. Exemplar radioimmunotherapy include ibritumomab (ZEVALIN) and tositumomab (BEXXAR). Radioisotope therapies (e.g., radioactive iodine, strontium, samarium, strontium-89, samarium ($^{153}$sm) lexidronam, and radium) are another type of systemic radiation used to treat certain types of cancers, such as thyroid, bone, and prostate cancers. Examples of radioisotope therapies include but are not limited to metaiodobenzylguanidine (MIBG), iodine-131, hormone-bound lutetium-177 and yttrium-90, yttrium-90 radioactive glass or resin microspheres, ibritumomab tiuxetan (Zevalin, an anti-CD20 monoclonal antibody conjugated to yttrium-90), tositumomab/iodine (131I) tositumomab regimen (BEXXAR, a combination of an iodine-131 labelled and an unlabelled anti-CD20 monoclonal antibody)

Radiation therapy dosages may be given in different ways, such as hyperfractionated radiotherapy and hypofractionated radiotherapy. In hyperfractionated radiotherapy, the total dose of radiation is divided into small doses and treatments are given more than once a day. Hyperfractionated radiation therapy is given over the same period of time (days or weeks) as standard radiation therapy. It is also called superfractionated radiation therapy. One type of hyperfractionated radiotherapy is continuous hyperfractionated accelerated radiotherapy (CHART). CHART without treatments at the weekends is called CHARTWEL. In hypofractionated radiotherapy, the total dose of radiation is divided into large doses and treatments are given once a day or less often. Hypofractionated radiation therapy is given over a shorter period of time (fewer days or weeks) than standard radiation therapy.

Surgical resection remains the only hope for long-term survival in pancreatic ductal adenocarcinoma (PDAC), yet 80% of patients with non-metastatic disease have unresectable tumors not likely to be down-staged following treatment with standard chemotherapy and radiotherapy. This is due to persistent involvement of local blood vessels by tumor. Overall survival rates in the 20% of patients undergoing margin negative resection after neoadjuvant therapy are 2-3 times that of those who remain unresectable underscoring the need to improve downstaging rates and refine diagnostic criteria to identify such patients. Radiation dose intensification strategies using SBRT have improved local control rates yet have resulted in disappointing rates of tumor downstaging largely due to inability to accurately assess the post-radiotherapy fibrotic tumor-vessel interaction using the triple-phase CT scan. Response Evaluation Criteria in Solid Tumors (RECIST) also inadequately characterize response of borderline resectable pancreatic tumors to radiotherapy, as exemplified by high rates of post-radiotherapy margin negative resections in spite of minimal radiographic changes identified on CT.

Programmed Cell Death-Ligand 1 (PD-L1/B7-H1) plays an important role in the negative regulation of cell-mediated immune responses through interactions with its receptor, programmed death-1 (PD-1). Overexpression of PD-L1 by tumor cells has been noted in a number of human cancers and shown to impair anti-tumor T-cell immunity. Indeed, subsequent blockade of this pathway has produced significant clinical responses in multiple cancers. To date, minimal data exists regarding the role of PD1-PDL1 in pancreatic ductal adenocarcinoma (PDA), which remains one of the most lethal solid tumors with a mortality to incidence ratio approximating 1. Long term survival is only achievable in patients who undergo definitive resection. Numerous studies have shown suboptimal clinical outcomes in patients undergoing incomplete (R1 or R2) resections for PDA, thus providing impetus to study novel radiotherapeutic strategies, such as stereotactic ablative body radiotherapy (SABR). Recent data suggest high likelihood of tumor control, downstaging and resectability with this strategy. Early data also suggests PD-L1 expression in PDA tissues may serve as a potential prognosticator of response to therapy. Additionally, blockade of PD-L1 in a mouse model of PDA has been shown to produce anti-tumor responses. Our immunohistochemical analysis of treatment of naïve pancreatic tumors reveals low level expression of PD-L1 in PDA. Biopsy samples from pancreatic tumors prior to treatment were also analyzed using RNASeq. While IFN-gamma levels at baseline are low in tumors, there is substantial STAT1 expression suggesting the potential for a rapid response to IFN-gamma leading to potential upregulation of PD-L1/2. Additionally, there is little PD-1 expression in tumors at baseline, but there is expression of PD-L1 and PD-L2 in all tumors highlighting the possibility that pancreatic tumors evade the immune system using PD-L1 mediated immunosuppression. These data suggest the importance of PD-L1 as both a potential prognostic marker and therapeutic target in PDA.

T cells play an important role in the anti-tumor efficacy of radiation (RT) as tumor-bearing mice lacking T cells need significantly more RT dose to achieve similar tumor control. Importantly, interferon-gamma, a cytokine known to upregulate PD-L1 expression on stromal cells such as fibroblasts and endothelial cells, is highly induced in the inflammatory response following RT). Our serologic analysis of PDA patients treated with RT revealed that levels of inflammatory markers (CRP, SAA, IL-6) increase significantly during RT by 4 weeks of treatment. This inflammatory response is consistent with our observed upregulation of PD-L1 in the pancreas. All patients demonstrated a similar inflammatory cytokine pattern suggesting a common pathway of inflammation in response to combined therapy. These results suggest there is a common and stereotyped response to RT that can be targeted to enhance anti-tumor inflammation. Additionally, analysis of FFPE archival tissue using quantitative immunohistochemistry of pre- and post-RT of locally advanced PDA patients reveals induction of PD-L1 likely in response to RT-mediated upregulation of interferon-gamma. Thus, without being bound by a particular theory, we hypothesize that upregulation of the PD-1-PD-L1 pathway mitigates the efficacy of RT in PDA. Indeed, this mechanism of adaptive immune resistance by PDA may serve as an ideal therapeutic target for combined RT and PD-L1 blockade. Given the potential therapeutic implications of PD-1 inhibition in pancreatic ductal adenocarcinoma (PDA), provided herein are methods of treating pancreatic cancer using a combination of durvalumab and SABR in patients with borderline resectable and locally advanced unresectable PDA.

Various embodiments provided herein include a method for treating cancer in a subject in need thereof. The method includes administering to the subject an effective amount of an agent that inhibits binding of PD-L1 to PD1 and an effective amount of radiotherapy. In various embodiments, the agent that inhibits binding of PD-L1 to PD1 and the radiotherapy are administered in a treatment regimen that includes periodically administering the agent that inhibits binding of PD-L1 to PD1, and on about day 8 (calculated from the day of the first dose of the agent that inhibits binding of PD-L1 to PD1) periodically administering the radiotherapy. The periodic schedule for the agent that inhibits binding of PD-L1 to PD1, and the periodic schedule for administering the radiotherapy are as provided herein.

In various embodiments, the agent is durvalumab. In an embodiment, the radiotherapy is SABR. In various embodiments, the durvalumab and SABR are administered simultaneously. In various embodiments, the durvalumab and SABR are administered sequentially. In some embodiments, the method includes providing a composition comprising an agent that inhibits binding of PD-L1 to PD1 (e.g., durvalumab).

Various embodiments provided herein include a method for preventing or reducing the likelihood of metastasis of cancer in a subject in need thereof. The method includes administering to the subject an effective amount of an agent that inhibits binding of PD-L1 to PD1 and an effective amount of radiotherapy.

In various embodiments, the agent that inhibits binding of PD-L1 to PD1 and the radiotherapy are administered in a treatment regimen that includes periodically administering the agent that inhibits binding of PD-L1 to PD1, and on about day 8 (calculated from the day of the first dose of the agent that inhibits binding of PD-L1 to PD1) periodically administering the radiotherapy. The periodic schedule for the agent that inhibits binding of PD-L1 to PD1, and the periodic schedule for administering the radiotherapy are as provided herein.

In various embodiments, the agent is durvalumab. In an embodiment, the radiotherapy is SABR. In various embodiments, the durvalumab and SABR are administered simultaneously. In various embodiments, the durvalumab and SABR are administered sequentially. In some embodiments, the method includes providing a composition comprising an agent that inhibits binding of PD-L1 to PD1 (e.g., durvalumab).

Further provided herein are methods for inhibiting, slowing progression of or reducing the severity of cancer in a subject in need thereof. The methods include administering to the subject an effective amount of an agent that inhibits binding of PD-L1 to PD1 and an effective amount of radiotherapy.

In various embodiments, the agent that inhibits binding of PD-L1 to PD1 and the radiotherapy are administered in a treatment regimen that includes periodically administering the agent that inhibits binding of PD-L1 to PD1, and on about day 8 (calculated from the day of the first dose of the agent that inhibits binding of PD-L1 to PD1) periodically administering the radiotherapy. The periodic schedule for the agent that inhibits binding of PD-L1 to PD1, and the periodic schedule for administering the radiotherapy are as provided herein.

In various embodiments, the agent is durvalumab. In an embodiment, the radiotherapy is SABR. In various embodiments, the durvalumab and SABR are administered simultaneously. In various embodiments, the durvalumab and SABR are administered sequentially. In some embodiments, the methods include providing a composition comprising an agent that inhibits binding of PD-L1 to PD1 (e.g., durvalumab).

In various embodiments, the agent that inhibits binding of PD-L1 to PD1 is a PD1 inhibitor and can be selected from the group consisting of pembrolizumab, nivolumab, pidilizumab, AMP-224, AMP-514, spartalizumab, cemiplimab, AK105, BCD-100, BI 754091, JS001, LZMO09, MGA012, Sym021, TSR-042, MGD013, AK104, XmAb20717, tislelizumab, PF-06801591, anti-PD1 antibody expressing pluripotent killer T lymphocytes (PIK-PD-1), autologous anti-EGFRvIII 4SCAR-IgT cells, and combinations thereof.

In various embodiments, the agent that inhibits binding of PD-L1 to PD1 is a PDL1 inhibitor and can be selected from the group consisting of BGB-A333, CK-301, FAZ053, KN035, MDX-1105, MSB2311, SHR-1316, atezolizumab, avelumab, durvalumab, BMS-936559, CK-301, M7824, and combinations thereof.

In various embodiments, the apparatus for administering a radiotherapy is a radiation machine or equipment, for example, those machines and systems used for focused radiotherapy, external beam radiation therapy, conventional external beam radiation therapy (2DXRT), image guided radiotherapy (IGRT), three-dimensional conformal radiation therapy (3D-CRT), intensity modulated radiation therapy (IMRT), helical tomotherapy, volumetric modulated arc therapy (VMAT), particle therapy, proton beam therapy, conformal proton beam radiation therapy, auger therapy (AT), stereotactic radiation therapy, stereotactic radiosurgery (SRS), stereotactic body radiation therapy (SBRT), stereotactic ablative body radiotherapy (SABR), brachytherapy, internal radiation therapy, intraoperative radiation therapy (IORT), radioimmunotherapy, radioisotope therapy, hyperfractionated radiotherapy, or hypofractionated radiotherapy. In various embodiments, the apparatus for administering a radiotherapy is a linear accelerator (often called a "linac" for short).

In various embodiments, the subject is a human. In various embodiments, the subject is a mammalian subject including but not limited to human, monkey, ape, dog, cat, cow, horse, goat, pig, rabbit, mouse and rat. In some embodiments, the subject is an animal model of pancreatic cancer. In some embodiments, the subject has pancreatic cancer.

In various embodiments, the cancer is pancreatic cancer, exocrine pancreatic cancer, pancreatic adenocarcinoma, acinar cell carcinoma, intraductal papillary-mucinous neoplasm (IPMN), mucinous cystadenocarcinoma, endocrine pancreatic cancer, pancreatic neuroendocrine tumor (pancreatic NET or PNET), gastrinoma, glucagonoma, insulinoma, somatostatinoma, VIPoma, nonfunctional islet cell tumor, resectable pancreatic cancer, locally advanced/unresectable pancreatic cancer, or metastatic pancreatic cancer, or a combination thereof. In various embodiments, the cancer is pancreatic cancer. In a further embodiment, the subject has borderline resectable and locally advanced unresectable PDA.

Also provided herein are methods for assessing efficacy of treatment for pancreatic cancer in a subject undergoing treatment using a combination of durvalumab and SABR as described herein. The methods include obtaining a sample from a subject and determining the level of biomarker for pancreatic cancer in the sample wherein a change in the level of biomarkers is indicative of efficacy of treatment. In various embodiments, the change is an increase in the level of the biomarkers. In various embodiments, the change is a decrease in the level of the biomarkers. Non-limiting examples of the biomarker of pancreatic cancer include but are not limited to CD24, ABCC3 and TLR2. More information can be found in Morse et al. 2010a (Identification of pancreatic cancer-specific cell-surface markers for development of targeting ligands, Methods Mol Biol. 2010; 624: 195-210) and Morse et al. 2010b (Identification of novel pancreatic adenocarcinoma cell-surface targets by gene expression profiling and tissue microarray, Biochem Pharmacol. 2010 Sep. 1; 80(5):748-54).

In various embodiments, the radiotherapy is focused radiotherapy, external beam radiation therapy, conventional external beam radiation therapy (2DXRT), image guided radiotherapy (IGRT), three-dimensional conformal radiation therapy (3D-CRT), intensity modulated radiation therapy (IMRT), helical tomotherapy, volumetric modulated arc therapy (VMAT), particle therapy, proton beam therapy, conformal proton beam radiation therapy, auger therapy (AT), stereotactic radiation therapy, stereotactic radiosurgery (SRS), stereotactic body radiation therapy (SBRT), brachytherapy, internal radiation therapy, intraoperative radiation therapy (IORT), radioimmunotherapy, radioisotope therapy, hyperfractionated radiotherapy, or hypofractionated radiotherapy, or a combination thereof.

Typical dosages of an effective amount of radiation to be administered to the subject can be in the ranges radiation biologist, radiation oncologist or medical physicist where known radiotherapy techniques are used, and also as indicated to the skilled artisan by the in vitro responses in cells or in vivo responses in animal models. The actual dosage can depend upon the judgment of the physician, the condition of the patient, and the effectiveness of the radiotherapy technique based, for example, on the in vitro responsiveness of relevant cultured cells or histocultured tissue sample, or the responses observed in the appropriate animal models. For example, mice models of pancreatic cancer may be subjected to focused radiotherapy using X-RAD small animal irradiator; appropriate parameters for radiotherapy are identified to maximize clinical outcomes these data serve as basis for translation to clinical trials and treatments in humans. In some embodiments of present invention, typical in vitro and in vivo doses may range from 50 cGy to 8 Gy daily fractions with total treatment doses ranging from 1 Gy to 50 Gy.

In various embodiments, the radiation dosage has a daily or every other day treatment dose of about 1-10, 10-20, 20-30, 30-40, 40-50, 50-60, 60-70, 70-80, 80-90, or 90-100 cGy. In various embodiments, the radiation dosage has a daily or every other day treatment dose of about 0.1-1, 1-2, 2-3, 1-3, 3-4, 4-5, 3-5, 5-6, 6-7, 5-7, 7-8, 8-9, 7-9 or 9-10 Gy.

In various embodiments, the radiation dosage has a total treatment dose of about 1-10, 10-20, 20-30, 30-40, 40-50, 50-60, 60-70, 70-80, 80-90, or 90-100 Gy. In various embodiments, the radiation dosage has a total treatment dose of about 0.1-1, 1-2, 2-3, 1-3, 3-4, 4-5, 3-5, 5-6, 6-7, 5-7, 7-8, 8-9, 7-9 or 9-10 Gy.

In various embodiments, a radiation dosage of about 4, 5, 6, 7, or 8 Gy per fraction is delivered every alternate day for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 fractions.

In various embodiments, a radiation dosage of about 4, 5, 6, 7, or 8 Gy per fraction is delivered every three days (i.e., two day break) for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 fractions.

In various embodiments, the SABR radiation dosage of about 4, 5, 6, 7, or 8 Gy per fraction is delivered every alternate day for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 fractions.

In various embodiments, the SABR radiation dosage of about 4, 5, 6, 7, or 8 Gy per fraction is delivered every three days for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 fractions.

In various embodiments, the SABR radiation dosage about 5-7Gy per fraction delivered every alternate day for about 5-7 fractions. In various embodiments, the SABR radiation dosage about 6.6 Gy per fraction delivered every alternate day for 5 fractions.

In some embodiments, treatment of cancer using, for example, durvalumab and SABR as described herein (or an agent that inhibits binding of PD-L1 to PD1 and radiation therapy) may be combined with further chemotherapeutic agents. In accordance with the present invention, examples of the chemotherapeutic agent include but are not limited to Temozolomide, Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, liposome-encapsulated Doxorubicin such as Doxil (pegylated form), Myocet (nonpegylated form) and Caelyx, Epirubicin, Epothilone, Erlotinib, Etoposide, Fluorouracil, Gefitinib, Gemcitabine, Hydroxyurea, Idarubicin, Imatinib, Ipilimumab, Irinotecan, Nanoliposomal Irinotecan (Nal-IRI), Mechlorethamine, Melphalan, Mercaptopurine, Methotrexate, Mitoxantrone, Ocrelizumab, Ofatumumab, Oxaliplatin, Paclitaxel, Protein-Bound Paclitaxel, Nab-Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof.

In various embodiments, the chemotherapeutic agent is a platinum-based antineoplastic agent. Examples of the platinum-based antineoplastic agent include but are not limited to oxaliplatin, cisplatin, lipoplatin (a liposomal version of cisplatin), carboplatin, satraplatin, picoplatin, nedaplatin, and triplatin.

In various embodiments, the chemotherapeutic agent is a taxane. Examples of the taxane include but are not limited to paclitaxel, docetaxel, and cabazitaxel. In certain embodiments, the chemotherapeutic agent is paclitaxel, or its functional equivalent, analog, derivative, variant or salt, or a combination thereof. In some embodiments, the chemotherapeutic agent is protein-bound paclitaxel or nab-paclitaxel.

In various embodiments, the chemotherapeutic agent is an anthracycline. Examples of the anthracycline include but are not limited to doxorubicin, daunorubicin, epirubicin, idarubicin, pirarubicin, aclarubicin, valrubicin, and mitoxantrone. In certain embodiments, the chemotherapeutic agent is doxorubicin, or its functional equivalent, analog, derivative, variant or salt, or a combination thereof.

Typical dosages of an effective amount of the agent that inhibits binding of PD-L1 to PD1 (e.g., durvalumab) can be in the ranges recommended by the manufacturer where known molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the agent that inhibits binding of PD-L1 to PD1 (e.g., durvalumab) may be administered once a day (SID/QD), twice a day (BID), three times a day (TID), four times a day (QID), or more, so as to administer an effective amount of the agent that inhibits binding of PD-L1 to PD1 (e.g., durvalumab) to the subject, where the effective amount is any one or more of the doses described herein.

In various embodiments, the effective amount of agent that inhibits binding of PD-L1 to PD1 (e.g., durvalumab) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg inhibitor/kg body weight, or a combination thereof. In various embodiments, the effective amount of agent that inhibits binding of PD-L1 to PD1 (e.g., durvalumab) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg inhibitor/m$^2$ body surface area, or a combination thereof. Here, "mg agent/kg body weight" refers to mg agent per kg body weight of the subject, and "mg agent/m$^2$ body surface area" refers to mg agent per m$^2$ body surface area of the subject. In certain embodiments, the agent is administered to a human. In some embodiments, the agent that inhibits binding of PD-L1 to PD1 (e.g., durvalumab) is administered in the amount of about 100 mg-1000 mg, 100 mg-900 mg, 100 mg-800 mg, 100 mg-700 mg, 100 mg-600 mg, 100 mg-500 mg, 100 mg-400 mg, 100 mg-300 mg, 100 mg-200 mg, 200 mg-800 mg, 300 mg-800 mg, 400 mg-800 mg, 500 mg-800 mg, 600 mg-800 mg, 700 mg-800 mg, 250 mg-500 mg, 250 mg-800 mg, 250 mg-1000 mg, 500 mg-1000 mg, 800 mg-1000 mg or combinations thereof, about every 1-21 days, 1-14 days, 1-10 days, 1-7 days, 1-5 days, 3-10 days, 5-10 days, 7-14 days, 7-21 days, 10-14 days, 10-21 days, 14-21 days or combinations thereof, for about 1-5 weeks, 5-7 weeks, 7-10 weeks, 10-12 weeks, or combinations thereof, or every 2 weeks or every 4 weeks.

In various embodiments, the agent that inhibits binding of PD-L1 to PD1 (e.g., durvalumab) is administered every 1, 2, 3, 4, 5, 6, 7, or 8 weeks.

In various embodiments, the agent that inhibits binding of PD-L1 to PD1 (e.g., durvalumab) is administered every 2 weeks or every 4 weeks.

In various embodiments, the effective amount of agent that inhibits binding of PD-L1 to PD1 (e.g., durvalumab) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of agent that inhibits binding of PD-L1 to PD1 (e.g., durvalumab) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/m$^2$/day, or a combination thereof. Here, "m/kg/day" or "mg/kg/day" refers to $_1$ µg or mg agent per kg body weight of the subject per day, and "m/m$^2$/day" or "mg/m$^2$/day" refers to 1 µg or mg agent per m$^2$ body surface area of the subject per day.

In accordance with the invention, the carrier may be administered using the appropriate modes of administration, for instance, the modes of administration recommended by the manufacturer for the carrier. In accordance with the invention, various routes may be utilized to administer the carrier of the claimed methods, including but not limited to intratumoral, intravascular, intravenous, intraarterial, intramuscular, subcutaneous, intraperitoneal, aerosol, nasal, via inhalation, oral, transmucosal, transdermal, parenteral, implantable pump or reservoir, continuous infusion, enteral application, topical application, local application, capsules and/or injections. In various embodiments, the carrier is administered intracranially, intraventricularly, intrathecally, epidurally, intradurally, topically, intratumorally, intravascularly, intravenously, intraarterially, intramuscularly, subcutaneously, intraperitoneally, intranasally, or orally.

In various embodiments, the agent that inhibits binding of PD-L1 to PD1 (e.g., durvalumab) is administered before, during and after radiation therapy (e.g., SABR).

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Given the potential therapeutic implications of PD-1 inhibition in PDA, described herein is the use of a combination of durvalumab and SABR in patients with pancreatic cancer.

List of abbreviations: (AE) Adverse Event; (ALT) Alanine Aminotransferase; (ALC) Absolute Lymphocyte Count; (AST) Aspartate Aminotransferase; (BUN) Blood Urea Nitrogen; (CBC) Complete Blood Count; (CMP) Comprehensive Metabolic Panel; (CR) Complete Response; (CT) Computed Tomography; (CTCAE) Common Terminology Criteria for Adverse Events; (DLT) Dose Limiting Toxicity; (DSMB) Data and Safety Monitoring Board; (ECOG) Eastern Cooperative Oncology Group; (H&P) History & Physical Exam; (HRPP) Human Research Protections Program; (IV (or iv)) Intravenously; (MTD) Maximum Tolerated Dose; (NCI) National Cancer Institute; (ORR) Overall Response Rate; (OS) Overall Survival; (PBMCs) Peripheral Blood Mononuclear Cells; (PD) Progressive Disease; (PFS) Progression Free Survival; (p.o.) per os/by mouth/orally; (PR) Partial Response; (SAE) Serious Adverse Event; (SD) Stable Disease; (SGOT) Serum Glutamic Oxaloacetic Transaminase; (SPGT) Serum Glutamic Pyruvic Transaminase; (WBC) White Blood Cells.

Study Objectives

Primary Objectives. Determine the safety and tolerability of durvalumab in combination with SABR in patients with borderline resectable and locally advanced pancreatic cancer. Measure clinical activity of durvalumab with SABR by assessing: a) rates of downstaging to resectability and b) progression free survival and c) overall survival.

Secondary Objectives. Evaluate pre/post-treatment core biopsies and pre/during/post-treatment blood for pathologic/immunologic markers, including but not limited to: Evaluate pre/post-treatment core biopsies and pre/during/post-treatment blood for pathologic/immunologic markers, including but not limited to: a) cytokine analysis from serum examining inflammatory cytokines: GM-CSF, IFNγ, IL-1β, IL-2, IL-6, IL-8, IL-10, IL-12, IL-15, IL-17, IL-18, TGF-beta, p70 and TNFα; b) immune cell profiling by flow cytometry from biopsies and blood: CD4+ T cells, CD8+ T cells, Regulatory T cells, B cells, NK cells, Gamma-Delta T Cells, macrophages/macrophage subsets (MDSC, iMC) and dendritic cells with activation markers including MHCII, CD25, CD62L, CD69, CD80; c) quantitative immunohistochemistry on biopsy samples: PD-L1, cleaved caspase 3, Ki-67, CD31; d) pre/post treatment stool studies for microbiome analysis; e) gene and RNA sequencing; f) both blood and biopsy samples will also be archived in our Biobank for future studies.

Patient Eligibility

Inclusion Criteria.

Patients with histolopathological or cytological diagnosis of adenocarcinoma of the pancreas, as well as those with high clinical suspicion of adenocarcinoma, which is deemed locally advanced unresectable or borderline resectable per NCCN guidelines or following evaluation by a Multidisciplinary group of physicians.

Patients must have received gemcitabine/nab-paclitaxel regimen prior to enrollment with at least stable disease by restaging imaging. Age>18 years. Body weight>30 kg. Karnofsky>80% (Table 7). Life expectancy of greater than 6 months, in the opinion of the investigator.

Patients must have normal organ and marrow function as defined below:

| | |
|---|---|
| Absolute Neutrophil Count (ANC) | >1,500/mcL |
| Platelets | >100,000/mcL |
| Hemoglobin | >9 g/dL |
| Total bilirubin | ≤1.5 × upper limit of normal (ULN) biliary stents |
| AST(SGOT) and ALT(SGPT) | <2.5 × ULN |
| Creatinine OR creatinine clearance | ≤1.5 times the upper limit of normal OR >40 mL/min for patients with creatinine levels above normal. |

Note:
Patients with biliary stent are eligible provided that all other inclusion criteria are met.

Treatment Plan-Treatment Dosage and Administration

The primary aim of this phase I/II trial is to determine safety and tolerability of this combination in patients with biopsy proven borderline resectable, or locally advanced unresectable pancreatic cancer. Patients identified to meet these criteria by a multidisciplinary team will receive standard of care (SOC) gemcitabine and abraxane chemotherapy for up to 6 months (Von Hoff et al, NEJM, 2013), followed by restaging. Patients with at least stable disease will be eligible for study treatment.

Patients will initiate durvalumab (750 mg Q14 days) on D1. SABR (6.6 Gy per fraction delivered every other day ×5 fractions) will begin D8. Durvalumab will continue as maintenance Q14 days (e.g., calculated from the initial administration of durvalumab) until resection or progression. Repeat endoscopic research biopsy of primary tumor will be obtained approximately 4-8 weeks post completion of SABR unless patient is deemed resectable and undergoes surgery which will allow analysis of resected specimens. Patients will undergo SOC imaging (CT chest, abdomen, pelvis ±PET) every 2 months for response assessment. Weekly blood samples will be obtained beginning D1 weeks 1-10 and every 2 months until resection or progression. Dose limiting toxicities (DLTs), adverse events (AEs) and serious adverse events (SAEs) will be assessed during the first 10 weeks of study treatment. This is a phase II trial with a run in phase I testing the safety of the combination. In the run in phase I, 3 patients will be enrolled at the fixed dose combination and if 2 or more DLTs are observed by the end of the first cycle, the trial will be terminated. If 1 or less DLTs are observed, another cohort of 3 patients is enrolled at this same dose combination. If 2 or more DLTs out of the 6 patients are observed after the first cycle, the trial is terminated. Otherwise, the phase II part proceeds including patients from the phase I run in phase.

Durvalumab: The investigational treatment cycle is 10 weeks during which time DLTs will be assessed. Treatment will be administered on an outpatient basis. Patients removed from study for unacceptable adverse events will be followed until resolution or stabilization of the adverse event. In addition, subjects will be evaluated for safety/toxicity during every visit and post-treatment imaging at week 8 and every 8 weeks thereafter, and as clinically indicated. Toxicity will be evaluated using the NCI Common Terminology Criteria for Adverse Events, Version 4.0. The frequency of toxicities per organ system will be tabulated using descriptive statistics. All patients who receive any amount of the study drug will be evaluable for toxicity.

Fiducial Placement and Biopsy: For use in tumor targeting, 3-5 gold radio-opaque fiducials will be placed intratumorally or peripheral to the tumor under endoscopic ultrasound guidance and simultaneously allow for research biopsy during the same procedure. If appropriate, fiducials may also be implanted intraoperatively.

Pre-Treatment Imaging, Motion Management: Patients will be simulated (and treated) supine with arms up using VacLoc immobilization. Arms will be placed at sides or on chest if physical limitations preclude arms up. Oral and intravenous contrast will be administered whenever appropriate to assist in the delineation of clinical target volumes as well as normal organs at risk. Respiratory motion will be managed with a combination of 4D CT, breath hold QFIX SDX, OSMS, or abdominal compression belt to minimize excursion. If patients must be treated free-breathing, an ITV-based planning technique will be used.

Target Volumes

GTV (gross tumor volume): primary tumor plus any radiographically involved regional lymph nodes, based on the CT (simulation), as well as standard diagnostic imaging (PET, CT, MR, etc.) obtained during the patient's staging work up.

CTV (clinical target volume): GTV+5 mm (isotropic), but limited by normal tissue boundaries.

PTV (planning target volume): CTV (or ITV if free breathing)+3 mm, unless a smaller PTV margin is appropriate based on clinical setup and motion management strategies in use.

Treatment Planning: Plans will be optimized using IMRT or VMAT techniques using the Varian Eclipse planning system. The PTV will receive 33 Gy (to a minimum of 95% of the PTV, e.g. V95) in 5 fractions, and the plans will be constrained to satisfy the normal tissue constraints (Table 1A) published by Herman [Herman SBRT study].

TABLE 1A

Normal Tissue Constraints

Spinal Cord + 5 mm max 0.5 cc < 25Gy
Proximal Duodenum and Stomach: 0.5 cc ≤ 30Gy, 5 cc ≤ 25 Gy
Bowel: same as duodenum/stomach
Liver 50% < 12 Gy
Combined Kidneys 75% < 12 Gy

Definition of Dose-Limiting Toxicity (DLT)

A DLT will be defined as any Grade 3 or higher treatment-related toxicity that occurs during the first 4 weeks of treatment, including: Any Grade 4 irAE; Any Grade 3 colitis; Any Grade 3 noninfectious pneumonitis irrespective of duration; Any≥Grade 2 pneumonitis that does not resolve to ≤Grade 1 within 7 days of the initiation of maximal supportive care; Any other Grade 3 irAE (excluding colitis or pneumonitis), that does not downgrade to Grade 2 within 7 days after onset of the event despite optimal medical management including systemic corticosteroids or does not downgrade to ≤Grade 1 or baseline within 14 days; Liver transaminase elevation >8×ULN or total bilirubin >5×ULN; Any ≥Grade 3 non-irAE, except for the exclusions listed below.

The definition excludes the following conditions: Grade 3 fatigue lasting ≤7 days; Grade 3 endocrine disorder (thyroid, pituitary, and/or adrenal insufficiency) that is managed with or without systemic corticosteroid therapy and/or hormone replacement therapy and the subject is asymptomatic; Grade 3 inflammatory reaction attributed to a local antitumor response (e.g., inflammatory reaction at sites of metastatic disease, lymph nodes); Concurrent vitiligo or alopecia of any AE grade; Grade 3 infusion-related reaction (first occurrence and in the absence of steroid prophylaxis) that resolves within 6 hours with appropriate clinical management; Grade 3 or 4 neutropenia that is not associated with fever or systemic infection that improves by at least 1 grade within 7 days. Grade 3 or Grade 4 febrile neutropenia will be a DLT regardless of duration or reversibility; Grade 3 or 4 lymphopenia; Isolated Grade 3 thrombocytopenia that is not associated with clinically significant bleeding and does not require medical intervention; Isolated Grade 3 electrolyte abnormalities that are not associated with clinical signs or symptoms and are reversed with appropriate maximal medical intervention within 3 days; Isolated Grade 3 amylase or lipase abnormalities that are not associated with clinical signs/symptoms or findings on imaging consistent with pancreatitis; Grade 3 nausea, vomiting, dehydration and diarrhea that resolves within 7 days with appropriate maximal medical intervention; Immune-related AEs are defined as events of immune nature (i.e., inflammatory) in the absence of a clear alternative etiology. In the absence of clinical abnormality, repeat laboratory testing will be conducted to confirm significant laboratory findings prior to designation as a DLT; An AE not listed above may be defined as a DLT after a consultation with the sponsor and investigators, based on the emerging safety profile.

Measurement Effect

Antitumor Effect-Solid Tumors.

Response and progression will be evaluated in this study using the new international criteria proposed by the Response Evaluation Criteria in Solid Tumors (RECIST) Committee [JNCI 92(3):205-216, 2000]. Changes in only the largest diameter (unidimensional measurement) of the tumor lesions are used in the RECIST v1.1 criteria.

Definitions.

Evaluable for toxicity. All patients will be evaluable for toxicity from the time of their first treatment with durvalumab.

Evaluable for objective response. Only those patients who have measurable disease present at baseline, have received at least one cycle of therapy, and have had their disease re-evaluated will be considered evaluable for response. These patients will have their response classified according to the definitions stated below. (Note: Patients who exhibit objective disease progression prior to the end of cycle 1 will also be considered evaluable.).

Disease Parameters

Measurable disease. Measurable lesions are defined as those that can be accurately measured in at least one dimension (longest diameter to be recorded) as >20 mm with conventional techniques (CT, MRI, x-ray) or as >10 mm with spiral CT scan. All tumor measurements must be recorded in millimeters (or decimal fractions of centimeters).

Note: Previously irradiated lesions are non-measurable except in cases of documented progression of the lesion since the completion of radiation therapy.

Non-measurable disease. All other lesions (or sites of disease), including small lesions (longest diameter <20 mm with conventional techniques or <10 mm using spiral CT scan), are considered non-measurable disease. Bone lesions, leptomeningeal disease, ascites, pleural/pericardial effusions, lymphangitis cutis/pulmonis, inflammatory breast disease, abdominal masses (not followed by CT or MRI), and cystic lesions are all non-measurable.

Target lesions. All measurable lesions up to a maximum of 3 lesions per organ and 6 lesions in total, representative of all involved organs, should be identified as target lesions and recorded and measured at baseline. Target lesions should be selected on the basis of their size (lesions with the longest diameter) and their suitability for accurate repeated measurements (either by imaging techniques or clinically). A sum of the longest diameter (LD) for all target lesions will be calculated and reported as the baseline sum LD. The baseline sum LD will be used as reference by which to characterize the objective tumor response.

Non-target lesions. All other lesions (or sites of disease) including any measurable lesions over and above the 6 target lesions should be identified as non-target lesions and should also be recorded at baseline. Measurements of these lesions are not required, but the presence or absence of each should be noted throughout follow-up.

Methods for Evaluation of Measurable Disease

All measurements should be taken and recorded in metric notation using a ruler or calipers. All baseline evaluations should be performed as closely as possible to the beginning of treatment and never more than 28 days before the beginning of the treatment.

The same method of assessment and the same technique should be used to characterize each identified and reported lesion at baseline and during follow-up. Imaging-based evaluation is preferred to evaluation by clinical examination when both methods have been used to assess the antitumor effect of a treatment.

Provide each method and note timeframe for when each will be done (e.g., every 6 weeks, every 2 cycles, etc.). Examples include:

Conventional CT and MM. These techniques should be performed with cuts of 10 mm or less in slice thickness contiguously. Spiral CT should be performed using a 5 mm contiguous reconstruction algorithm. This applies to tumors of the chest, abdomen, and pelvis.

Cytology, Histology. These techniques can be used to differentiate between partial responses (PR) and complete responses (CR) in rare cases (e.g., residual lesions in tumor types, such as germ cell tumors, where known residual benign tumors can remain).

The cytological confirmation of the neoplastic origin of any effusion that appears or worsens during treatment when the measurable tumor has met criteria for response or stable disease is mandatory to differentiate between response or stable disease (an effusion may be a side effect of the treatment) and progressive disease.

Response Criteria

Evaluation of Target Lesions.

Complete Response (CR): Disappearance of all target lesions, determined by two separate observations conducted not less than 4 weeks apart. There can be no appearance of new lesions.

Partial Response (PR): At least a 30% decrease in the sum of the longest diameter (LD) of target lesions, taking as reference the baseline sum LD. There can be no appearance of new lesions.

Progressive Disease (PD): At least a 20% increase in the sum of the LD of target lesions, taking as reference the smallest sum LD recorded since the treatment started, or the appearance of one or more new lesions.

Stable Disease (SD): Neither sufficient shrinkage to qualify for PR nor sufficient increase to qualify for PD, taking as reference the smallest sum LD since the treatment started.

Evaluation of Non-Target Lesions.

Complete Response (CR): Disappearance of all non-target lesions and normalization of tumor marker level.

Incomplete Response/Stable Disease (SD): Persistence of one or more non-target lesion(s) and/or maintenance of tumor marker level above the normal limits.

Progressive Disease (PD): Appearance of one or more new lesions and/or unequivocal progression of existing non-target lesions.

Evaluation of Best Overall Response.

The best overall response is the best response recorded from the start of the treatment until disease progression/recurrence (taking as reference for progressive disease the smallest measurements recorded since the treatment started). The patient's best response assignment will depend on the achievement of both measurement and confirmation criteria.

| Target Lesions | Non-Target Lesions | New Lesions | Overall Response | Best Response for this Category Also Requires: |
|---|---|---|---|---|
| CR | CR | No | CR | >4 wks. confirmation |
| CR | Non-CR/Non-PD | No | PR | >4 wks. confirmation |
| PR | Non-PD | No | PR | |
| SD | Non-PD | No | SD | documented at least once >4 wks. from baseline |
| PD | Any | Yes or No | PD | no prior SD, PR or CR |
| Any | PD* | Yes or No | PD | |
| Any | Any | Yes | PD | |

In exceptional circumstances, unequivocal progression in non-target lesions may be accepted as disease progression.
Note:
If subjects respond to treatment and are able to have their disease resected, the patient's response will be assessed prior to the surgery.

Duration of Response

Duration of overall response: The duration of overall response is measured from the time measurement criteria are met for CR or PR (whichever is first recorded) until the first date that recurrent or progressive disease is objectively documented (taking as reference for progressive disease the smallest measurements recorded since the treatment started).

The duration of overall CR is measured from the time measurement criteria are first met for CR until the first date that recurrent disease is objectively documented.

Duration of stable disease: Stable disease is measured from the start of the treatment until the criteria for progression are met, taking as reference the smallest measurements recorded since the treatment started.

Progression-Free Survival

Progression-free survival (PFS) is defined as the duration of time from start of treatment to time of progression.

Safety/Tolerability

Analyses will be performed for all patients having received at least one dose of durvalumab. The study will use the CTCAE version 4.0 for reporting of non-hematologic adverse events (http://ctep.cancer.gov/reporting/ctc.html) and modified criteria for hematologic adverse events.

Correlatives/Special Studies

Blood samples, flash frozen and formalin fixed tumor tissue will be collected for each patient.

Laboratory Correlative Studies

Interrogating the Tumor Microenvironment.
Rationale. Prospectively collected tumor tissue and blood samples will be interrogated using standard gene, RNA and protein profiling as follows:

ECM and Angiogenesis Profiling

Quantitative immunohistochemistry for collagen I, fibronectin, HA, dermatan sulfate, keratin sulfate, pancreatic stellate cells (CD10+, CD10− subpopulations), periostin, alpha SMA, HIF-1, VEG-F, FGF-2, angiopoietin-1.

Immune Profiling cytokine analysis from serum examining inflammatory cytokines: GM-CSF, IFNγ, IL-β, IL-2, IL-6, IL-8, IL-10, IL-12, IL-15, IL-17, IL-18, TGF-beta, p70 and TNFα;
immune cell profiling by flow cytometry from biopsies and blood: CD4+ T cells, CD8+ T cells, Regulatory T cells, B cells, NK cells, Gamma-Delta T Cells, macrophages/macrophage subsets (MDSC, iMC) and dendritic cells with activation markers including MHCII, CD25, CD62L, CD69, CD80;
quantitative immunohistochemistry on biopsy samples: PD-L1, cleaved caspase 3, Ki-67, CD31;
pre/post treatment stool studies for microbiome analysis;
gene and RNA sequencing;
both blood and biopsy samples will also be archived in our Biobank for future studies.

Collection of Specimens

Biopsy: If consent for enrollment is obtained prior to initial diagnostic biopsy (EGD or CT-guided), this core/fine needle aspiration biopsy specimen will be utilized for laboratory correlative studies. Otherwise, biopsy specimen for correlative studies will be obtained at time of fiducial placement. Tissue will obtained from fine needle aspiration using either a 19-22 gauge or 25 gauge needle. Alternatively, tissue will be obtained via core biopsy using a 19-22 gauge needle. Approximately 2-4 passes will be made until adequate specimen is obtained.

PD-L1 Testing

Testing should be restricted to the Ventana SP263 assay and should be performed in accordance with the package insert on the Ventana Benchmark platform (Ultra or XT). The Ventana SP263 assay is fully analytically validated test characterized through to the completion of reader precision studies in the non-small cell lung cancer (NSCLC) and squamous cell carcinoma of the head & neck (SCCHN). For these tumors, the Ventana SP263 assay has a full reproducibility data package supporting cut-off and scoring algorithm. Following completion of ATLANTIC and HAWK clinical trials, the assay will be associated with clinical utility. In other cancer types (bladder, pancreatic, gastric, hepatocellular, triple negative breast, ovarian, esophageal, nasopharyngeal, glioblastoma, soft tissue sarcoma, cholangiocarcinoma, small cell lung, melanoma and cervical HPV+ cancers), the Ventana SP263 assay has only limited clinical performance data.

Sample Collection for PD-L1 Testing

The preferred tumor sample for the determination of a patient's PD-L1 status is the one taken following the completion of the most recent prior line of therapy. Samples taken at this time reflect the current PD-L1 status of the tumor and considered clinically most relevant.

In previous studies, the preferred sample for PD-L1 testing was less than or equal to 3 months old. In cases where a sample a less than 3 months old was not available, patients were asked to undergo a new biopsy if considered clinically appropriate by their treating physician.

Samples should be collected via a core needle of 18 gauge or larger or be collected by an incisional or excisional tumor biopsy. Where institutional practice uses a smaller gauge needle, samples should be evaluated for tumor cell quantity (i.e. >100 tumor cells) to allow for adequate PD-L1 immunohistochemistry analyses.

When the collection of a new sample is not clinically appropriate, archival samples may be utilized provided the specimen it is not older than 3 years of age. When archival samples are used to assess PD-L1 status, the age of the sample/date of collection should be captured.

Samples submitted for PD-L1 testing should be formalin fixed and embedded in paraffin. Samples from fine needle aspirates (FNA) or decalcified bone are not appropriate for PD-L1 analysis.

Sample Data Collection for PD-L1 Testing

The following fields of data should be collected from the site/institution collecting and if, indicated shipping of the samples: Patient identifier (ecode or unique identifier); Specimen identifier (written on the specimen); Site identifier; Specimen collection date; Type of specimen submitted; Quantity of specimen; Date of sectioning; Archival of fresh tumor; Tumor type; Primary tumor location; Fixative.

The following fields of data should be collected from PD-L1 testing laboratory: Are the negative and positive controls stained correctly; Is the H&E material acceptable; Is morphology acceptable; Total percent positivity of PD-L 1 in tumor cells; PD-L 1 status (positive, negative or NA) in tumor cells; Total percent positivity of PD-L1 in infiltrating immune cells; Sample processing and if indicated submission process for PD-L1 testing.

Preparing Stored Samples for Testing

Where samples already exist, they should be retrieved from the Bio-Bank storage location. These blocks should undergo quality review, prior to evaluation or shipment. Where it is not possible or indicated to ship the block to a testing laboratory, unstained slides should be prepared from the paraffin-embedded tumor sample block (described below) prior to evaluation or shipment.

Preparing Newly Acquired Samples for PD-L1 Testing

If patients are undergoing a biopsy procedure that provides the option to submit newly acquired samples, this sample should be used to determine PD-L1 status. Where clinically acceptable, a minimum of 2 core biopsies should be collected and processed to FFPE in a single block. The provision of 2 cores is advised in order to provide sufficient tissue for PD-L1 assessment.

It is recommended that core needle tumor biopsies are collected using an 18 gauge or larger needle and the process should be image-guided. Excisional or incisional samples are also adequate. If this is not per the institutions normal practice and a smaller gauge needle is used then the number of cores collected should be increased to allow sufficient material for successful PD-L1 testing (>100 tumor cells) and embedded in the same block. If available, a single excisional biopsy of at least 4 mm in diameter may substitute for all core biopsies.

Fixation of Biopsy Samples for PD-L1 Testing

Previously frozen tissue is not acceptable for processing to FFPE for PD-L1 testing. To fix newly acquired tissue, place immediately (within 30 min of excision) into an adequate volume of 10% v/v neutral buffered formalin (NBF). Samples should remain in fixative for 24-48 hours at room temperature.

It is vital that there is an adequate volume of fixative relevant to the tissue (at least a 10 volume excess) and that large specimens (if any) are incised prior to fixation to promote efficient tissue preservation.

Embedding in Paraffin for PD-L1 t-Testing

An overnight processing schedule into paraffin wax is recommended. Storage of tumor blocks for PD-L1 testing. FFPE blocks should be stored at ambient temperature and protected from light until shipment by courier at ambient temperature. FFPE blocks are stable under these conditions for an indefinite period.

Quality Control of Samples To Be Used for PD-L1 Testing

Tissue should be assessed by the site pathologist prior to PD-L1 testing. Each sample should be reviewed for: Adequate fixation; Good preservation of morphology; Presence of tumor tissue; Histopathology consistent with indication.

Greater than 100 tumor cells are required to determine PD-L1 status—tumor cell content must be reviewed prior to testing in order for PD-L1 obtain a valid result.

If indicated, shipping samples to a PD-L1 testing laboratory.

When submitting sample to for PD-L1 testing the recommendation is to ship the block in order for sectioning to occur at the laboratory. Blocks should be shipped—containing enough material to be provided to allow a minimum of 5, and preferably 10, sections to be cut (each 4 micron thick) to be used for PD-L1 testing.

Blood: Two extra tubes of blood (EDTA preserved with anticoagulant—10 mL) will be drawn once a week during the evaluation period along with the patient's regular labs for research purposes.

Handling of Specimens

Half of the biopsy specimen will be snap frozen in liquid nitrogen within 30 minutes of performing biopsy to minimize tissue anoxia; specimen will be frozen long-term at −80° C. in cryovials. The remaining specimen will be fixed in 4% paraformaldehyde.

Immediately after collection, blood will be centrifuged and plasma collected and aliquoted for storage at −80° C.

Analysis of Specimen(s)

Frozen tissue specimen will be processed for DNA/protein extraction and isolation; formalin-fixed tissues will be paraffin embedded and sectioned. DNA damage repair proteins will be quantitated using Western, ELISA and immunohistochemistry.

Statistical Considerations

Study Design/Study Endpoints
Statistical Design
This is a phase II trial with a run in phase I testing the safety of the combination. In the run in phase I, 3 patients will be enrolled at the fixed dose combination and if 2 or more DLTs are observed by the end of the first cycle, the trial will be terminated. If 1 or less DLTs are observed, another cohort of 3 patients is enrolled at this same dose combination. If 2 or more DLTs out of the 6 patients are observed after the first cycle, the trial is terminated. Otherwise, the phase II part proceeds including patients from the phase I run in phase.

The primary objective of the phase II trial is PFS. The most recent phase 3 study in this setting showed a median PFS of 9 months. Therefore, data from a total of 30 patients achieve 81% power to detect an improvement in median PFS of 6 months (an increase from 9 months to 15 months) using a one-sided test at the 0.05 level of significance assuming an exponential distribution for time to progression, total accrual time of 30 months and 18 months of follow-up.

Stopping Rules.

For the phase II part, we compute the posterior probability that the DLT rate exceeds 40% given the data continuously assuming a uniform prior distribution for the rate of DLT. If this posterior probability is more than 0.7, we stop the trial for safety.

Secondary objectives: Kaplan-Meier estimators for the progression free survival (PFS) and overall survival (OS) will be obtained with 95% confidence bands. An exact 95% confidence interval will be constructed for the true rate of resectability and radiation response.

Paired t-tests will be used to test for differences in biomarkers from pre/post-treatment core biopsies and blood samples using a 0.01 level of significance due to the large number of markers. Statistically significant markers will be correlated with time to progression and overall survival using a Cox proportional hazards model. Due to the small sample size from the phase II trial and the potentially lack of post-treatment core biopsy in some patients, these studies will be purely exploratory.

We model the dose-toxicity-covariate relationship using the logistic model $$P(DLT \mid x, z_1, z_2) = \frac{\exp(\beta_0 + \beta_1 x + \eta_1 z_1 + \eta_2 z_2)}{1 + \exp(\beta_0 + \beta_1 x + \eta_1 z_1 + \eta_2 z_2)}, \quad (1.1)$$

where x is the dose, $z_1$ and $z_2$ are baseline covariate values such that $z_1=1$, $z_2=0$ corresponds to a patient falling in bin 1, $z_1=0$, $z_2=1$ corresponds to a patient falling in bin 2, and $z_1=0$, $z_2=0$ corresponds to a patient falling in bin 3 ($z_3=1$). Suppose doses are standardized in the interval [0, 1] using the transformation $h(u)=(u-30)/(50-30)=(u-30)/20$. We reparameterize the model in terms of parameters the clinician (PI) can easily interpret and are mathematically convenient to place vague prior distributions. These are $\rho03$, the probability of DLT when $x=0$ and $z_1=0$, $z_2=0$, that is the patient belongs to bin 3, $\rho01$, the probability of DLT when $x=0$ and $z_1=1$, $z_2=0$, $\rho02$, the probability of DLT when $x=0$ and $z_1=0$, $z_2=1$, and $\rho11$, the probability of DLT when $x=1$ and $z_1=1$, $z_2=0$. It can be shown that this is a one-to-one transformation:

$$\begin{cases} \beta_0 = logit(\rho_{03}) \\ \beta_1 = logit(\rho_{11}) - logit(\rho_{01}) \\ \eta_1 = logit(\rho_{01}) - logit(\rho_{03}) \\ \eta_2 = logit(\rho_{02}) - logit(\rho_{03}) \end{cases}. \quad (1.2)$$

The restriction on treatment tolerability based on the bins the restriction that $\gamma(z1) > \gamma(z2) > \gamma(z3)$ and the fact that the probability of DLT is an increasing function of dose imply that $0 \le \rho_{01} \le \rho_{02} \le \rho_{03}$ and $0 \le \rho_{01} \le \rho_{11}$. \quad (1.3)

Vague prior distributions were placed on these parameters by assuming that ρ03 and p11 are independent Unif(0,1), given ρ03, ρ02 Unif(0, ρ03), and given ρ02 and ρ11, ρ01 ~Unif(0, min{ρ02, ρ11}). We used JAGS and R to estimate features of the posterior distributions of the model parameters and establish design operating characteristics for the trial design described below.

Algorithm:
1. The first patient receives the minimum available dose 30 Gy regardless of the value of the baseline covariate z.
2. After the i-th patient is treated and his/her DLT status is resolved, let $\Pi_{z,i}$ be the marginal posterior cdf of the MTD $\gamma(z)$ given the data. The (i+1)st patient with covariate value $z_{i+1}$ receives the dose so that the posterior probability of exceeding the MTD $\gamma(z_{i+1})$ is equal to the feasibility bound $\alpha$.
3. Repeat steps 2 until a total of n patients have been accrued subject to the stopping rule defined below.

Stopping rule: Any time prior to enrollment of a prospective patient and after the first three patients have been enrolled, we stop enrollment to a bin if there is evidence that the posterior probability of DLT at the minimum dose available in the trial is excessively toxic. Specifically, we stop the trial is for given covariate value z, $$P(P(\text{DLT}|x=0,z) > \theta + 0.1 | \text{data}) > 0.75.$$

In step 2, the posterior distribution of the MTD given covariate value z is estimated using the MCMC sample of the model parameters by noting that reparameterization (1.2) and the definition of the MTD implies that the MTDs in each bin are $$\gamma(1) = \frac{logit(\theta) - logit(\rho_{01})}{logit(\rho_{11}) - logit(\rho_{01})} \quad (1.4)$$

$$\gamma(2) = \frac{logit(\theta) - logit(\rho_{02})}{logit(\rho_{11}) - logit(\rho_{01})}$$

$$\gamma(3) = \frac{logit(\theta) - logit(\rho_{03})}{logit(\rho_{11}) - logit(\rho_{01})}.$$

Design Operating Characteristics: We studied the operating characteristics of this design under three scenarios for the true values of the MTDs for each bin by simulating m=1000 trials. In each case, the trial sample size n=30 and 10 patients per bin are expected to be enrolled. Table 1 lists the three scenarios along with the true values of the model parameters. In scenario 1, the three MTDs are within the range of available doses in the trial, a scenario expected by the PI. In scenario 2, the MTD for patients in bin 1 fall outside the range of doses from above and in scenario 3, the MTD for patients in bin 3 is below the minimum dose available in the trial, 30 Gy.

TABLE 1

Three scenarios for the true values of the MTDs.

| | gamma_1 | gamma_2 | gamma_3 | rho_01 | rho_02 | rho_03 | rho_11 |
|---|---|---|---|---|---|---|---|
| Scenario 1 | 45 | 40 | 35 | 0.005 | 0.022 | 0.097 | 0.7 |
| Scenario 2 | 55 | 45 | 40 | 0.062 | 0.129 | 0.182 | 0.25 |
| Scenario 3 | 40 | 35 | 25 | 0.097 | 0.188 | 0.519 | 0.7 |

Table 2 gives the percent of trials that stop enrollment to the corresponding bin due to excessive toxicity as defined by the stopping rule in the above algorithm. We can see that in scenario 3, there is a 62.5% probability of stopping enrollment to bin 3. This is expected since the true MTD is 5 units below the minimum dose. The probability of stopping enrollment in the other bins in the other scenarios is either 0 or negligible.

TABLE 2

Percent of trials that stop early due to excessive number of toxicity.

| | rho_01 | rho_02 | rho_03 | rho_11 | % (B1) | % (B2) | % (B3) |
|---|---|---|---|---|---|---|---|
| scenario01 | 0.005 | 0.022 | 0.097 | 0.7 | 0 | 0 | 1.0 |
| scenario02 | 0.062 | 0.129 | 0.182 | 0.25 | 0 | 0 | 3.0 |
| scenario03 | 0.097 | 0.188 | 0.519 | 0.7 | 0 | 2.61 | 62.5 |

Tables 3 and 4 give the average percent of DLTs across all trials and the percent of trials that result in an excessive number of DLTS, respectively. Since the target probability of DLT is θ=0.33, we can say that the trial is safe except for scenario 3, bin 3, but there is a high probability of stopping enrollment to that bin early on. In fact, the average number of patients it takes to stop enrollment to that bin is 4.95.

TABLE 3

Average percent of DLTs across all trials

| | B1 | B2 | B3 | Overall |
|---|---|---|---|---|
| scenario01 | 0.42 | 0.20 | 0.13 | 0.25 |
| scenario02 | 0.23 | 0.24 | 0.21 | 0.23 |
| scenario03 | 0.40 | 0.23 | 0.54 | 0.39 |

TABLE 4

Percent of trials: DLT rate > θ + 0.10

| | B1 | B2 | B3 | Overall |
|---|---|---|---|---|
| scenario01 | 30.0 | 0.5 | 1.0 | 10.5 |
| scenario02 | 3.3 | 2.7 | 4.4 | 3.47 |
| scenario03 | 31.4 | 3.4 | 68.7 | 34.5 |

Table 5 gives the estimate of the true MTD defined as the average of all estimated MTDs from all m=1000 trials. We can see that in the ideal scenario (scenario 1), the average MTD is very close to the true MTD. This is also reflected by the average bias in Table 6. The average bias is slightly higher in scenarios 2 and 3. This is expected because in scenario 2, the true MTD for bin 1 is 55, higher than the maximum available dose in the trial and the dose escalation in that bin was bounded by 50. In scenario 3, bin 2 and 3 are still doing well since enrollment to bin 3 stops in about 63% of the trials. We conclude that the design has good operating characteristics in terms of both safety and efficiency of the estimated MTD.

TABLE 5

Estimates of the true MTD

|  | gamma_01 | gamma_02 | gamma_03 | B1 | B2 | B3 |
| --- | --- | --- | --- | --- | --- | --- |
| scenario01 | 45 | 40 | 35 | 45.7 | 39.18 | 33.06 |
| scenario02 | 55 | 45 | 40 | 49.35 | 43.48 | 33.58 |
| scenario03 | 40 | 35 | 25 | 40.88 | 32.57 | 30.01 |

TABLE 6

Average bias relative the true MTD

|  | gamma_01 | gamma_02 | gamma_03 | B1 | B2 | B3 |
| --- | --- | --- | --- | --- | --- | --- |
| scenario01 | 45 | 40 | 35 | 0.699 | −0.818 | −1.935 |
| scenario02 | 55 | 45 | 40 | −5.65 | −1.518 | −6.416 |
| scenario03 | 40 | 35 | 25 | 0.877 | −2.427 | 5.014 |

TABLE 7

Performance Status Criteria
Karnofsky Performance Scale

| Percent | Description |
| --- | --- |
| 100 | Normal, no complaints, no evidence of disease. |
| 90 | Able to carry on normal activity: minor signs or symptoms of disease. |
| 80 | Normal activity with effort: some signs or symptoms of disease. |
| 70 | Cares for self, unable to carry on normal activity or to do active work. |
| 60 | Requires occasional assistance, but is able to care for most of his/her needs. |
| 50 | Requires considerable assistance and frequent medical care. |
| 40 | Disabled, requires special care and assistance. |
| 30 | Severely disabled, hospitalization indicated. Death not imminent. |
| 20 | Very sick, hospitalization indicated. Death not imminent. |
| 10 | Moribund, fatal processes progressing rapidly. |
| 0 | Dead. |

Example 2

Based on prospective randomized clinical trials conducted in patients with locally advanced/borderline resectable pancreatic cancer, historical rates of progression free survival (PFS) and overall survival in patients treated with standard of care chemotherapy and chemoradiotherapy range from 6-9 months and 11-16 months.

To date, we have treated 10 locally advanced/borderline resectable pancreatic cancer patients with chemotherapy and the novel combination of SBRT/durvalumab. Of these patients, only 3 have progressed with PFS rates of 9, 12 and 13 months while others have at least stable disease. Six of ten with adequate follow up have survived at least 12 months and most have at least stable disease.

TABLE 8

Durvarad-A Phase 1/2 Study of Durvalumab and SABR in Locally Advanced Pancreatic Cancer

| ID | LA or BR Status | Date of Dx | On Study Date | Gem/ A (#) | D1 SBRT | Recist 2 mo | 4 mo | 6 mo |
| --- | --- | --- | --- | --- | --- | --- | --- | --- |
| 1 | LA on follow up | Apr. 17, 2017 | Sep. 6, 2017 | 5 | Sep. 11, 2017 | PR | PR | SD |
| 2 | not eligible | | | | | | | |
| 3 | withdrawn | | | | | | | |
| 4 | LA on follow up | Apr. 13, 2017 | Nov. 1, 2017 | 6 | Nov. 6, 2017 | SD | SD | PD |
| 5 | LA on follow up | Apr. 4, 2017 | Nov. 1, 2017 | 6 | Nov. 6, 2017 | PD | — | SD |
| 6 | withdrawn | | | | | | | |
| 7 | BR on follow up | Jul. 4, 2017 | Jan. 19, 2018 | 4 | Jan. 31, 2018 | SD | PR | NED |
| 8 | BR on follow up | Jun. 16, 2017 | Jan. 29, 2018 | 5 | Feb. 5, 2018 | SD | PR | TBD |
| 9 | LA on follow up not eligible | Jul. 26, 2017 | Mar. 7, 2018 | 4 | Mar. 14, 2018 | SD | TBD | TBD |
|  | LA on treatment | Jan. 16, 2018 | May 30, 2018 | 4 | Jun. 13, 2018 | TBD | TBD | TBD |
|  | LA on treatment | Dec. 20, 2017 | Jun. 2, 2018 | 4 | Jun. 13, 2018 | TBD | TBD | TBD |

TABLE 8-continued

Durvarad-A Phase 1/2 Study of Durvalumab and SABR in Locally Advanced Pancreatic Cancer

| | | | | | | | |
|---|---|---|---|---|---|---|---|
| BR on treatment | Mar. 12, 2018 | Jul. 16, 2018 | 4 | Jul. 23, 2018 | TBD | TBD | TBD |
| LA on treatment | Jan. 27, 2018 | Jul. 18, 2018 | 3 | TBD | TBD | TBD | TBD |
| LA consented | Mar. 14, 2018 | TBD | 3 | TBD | TBD | TBD | TBD |

| ID | 9 mo | 12 mo | Time from Dx (mo) | Time from Study Start (mo) | Post Tx Biopsy | Resected (date) | Off Study Date | PFS (mo) | Notes |
|---|---|---|---|---|---|---|---|---|---|
| 1 | PD | TBD | 15 | 10 | Y | N | May 31, 2018 | 13 | local progression only |
| 2 | | | | | | | | | |
| 3 | | | | | | | | | |
| 4 | TBD | TBD | 15 | 8 | Y | N | Apr. 17, 2018 | 12 | sd at primaly and liver mets |
| 5 | SD | TBD | 15 | 8 | N | N | Jan. 17, 2018 | 9 | sd at primaly; cr of bone met |
| 6 | | | | | | | | | |
| 7 | TBD | TBD | 12 | 6 | Y | Y (Apr. 25, 2018) | May 25, 2018 | NA | ypt2n0; trg 2 |
| 8 | TBD | TBD | 13 | 5 | Y | Y (Apr. 14, 2018) | May 14, 2018 | NA | ypt2n0; trg 2 |
| 9 | TBD | TBD | 11 | 4 | Y | Y (Jul. 6, 2018) | Jul. 6, 2018 | NA | ypt2n1; trg 2 |
| | TBD | TBD | 6 | 1 | TBD | TBD | | NA | |
| | TBD | TBD | 7 | 1 | TBD | TBD | | NA | |
| | TBD | TBD | 4 | 0 | TBD | TBD | | NA | |
| | TBD | TBD | 5 | 0 | TBD | TBD | | NA | |
| | TBD | TBD | 4 | 0 | TBD | TBD | | NA | |

SABR/SBRT: Stereotactic Ablative Radiotherapy
LA: locally advanced
BR: borderline resectable
PR: Partial response
SD: stable disease
PD: Progressive disease
CR: complete response Example 3

A cancer patient (e.g., pancreatic cancer) is administered about 500-1000 mg durvalumab. The patient continues to be administered about 500-1000 mg durvalumab about every 1-5 weeks for 20-30 doses. After the first dose of durvalumab, about 6-7 Gy per fraction delivered 5-7 fractions of SABR is administered every 1-3 days to the patient. At times the durvalumab can overlap with SABR.

Example 4

A cancer patient (e.g., pancreatic cancer) is given intravenous administration of about 750 mg durvalumab. The patient continues to be administered about 750 mg durvalumab (IV) about every two weeks or about every 4 weeks for 25 doses. After the first dose of durvalumab, about 6.6 Gy per fraction delivered in five fractions of SABR is administered to the patient. At times the durvalumab can overlap with SABR.

Example 5

A cancer patient (e.g., pancreatic cancer) is administered about 500-1000 mg durvalumab and about 0.5-1.5 mg/kg tremelimumab (formerly ticilimumab, CP-675,206). The patient continues to be administered about 500-1000 mg durvalumab about every 1-5 weeks for 20-30 doses, and is administered about 0.5-1.5 mg/kg tremelimumab every 3-5 weeks for 2-4 doses. After the first dose of durvalumab, about 6-7 Gy per fraction delivered 5-7 fractions of SABR is administered every 1-3 days. At times the durvalumab can overlap with SABR.

Example 6

A cancer patient (e.g., pancreatic cancer) is given intravenous administration of about 750 mg durvalumab and about 1 mg/kg tremelimumab. The patient continues to be administered about 750 mg durvalumab (IV) about every two weeks or every four weeks for 25 doses, and is administered 1 mg/kg tremelimumab every 4 weeks for three doses. After the first dose of durvalumab, about 6.6 Gy per fraction delivered in five fractions of SABR is administered. At times the durvalumab can overlap with SABR.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of treating pancreatic cancer in a subject, comprising:
    administering to the subject an effective amount of durvalumab; and
    administering to the subject an effective dosage of stereotactic body radiation therapy (SBRT),
    thereby treating the pancreatic cancer in the subject.

2. The method of claim 1, wherein the SBRT is used in conjunction with image guided radiotherapy (IGRT), image guided radiotherapy (IGRT), volumetric modulated arc therapy (VMAT), or a combination thereof.

3. The method of claim 1, wherein the subject is a human.

4. The method of claim 1, wherein the subject has borderline resectable or locally advanced unresectable pancreatic ductal adenocarcinoma (PDA).

5. The method of claim 1, wherein the durvalumab is administered in the amount of about 100 mg-1000 mg.

6. The method of claim 1, wherein the durvalumab is administered in an amount of about 750 mg.

7. The method of claim 1, wherein the durvalumab is administered about every 1-5 weeks.

8. The method of claim 1, wherein the durvalumab is administered about every 14 days.

9. The method of claim 1, wherein the durvalumab is administered about every 28 days.

10. The method of claim 1, wherein the durvalumab is administered for about 2-50 weeks.

11. The method of claim 1, wherein the durvalumab is administered for about 10-50 weeks.

12. The method of claim 1, wherein the stereotactic body radiation therapy (SBRT) is administered at a dosage of about 5-7Gy per fraction delivered about every alternate day for 5-7 fractions.

13. The method of claim 1, wherein the stereotactic body radiation therapy (SBRT) is administered at a dosage of about 6.6Gy per fraction delivered about every alternate day for 5 fractions.

14. The method of claim 1, wherein the durvalumab is administered about every 14 days or about every 28 days, and the SBRT is administered starting on about day 8, calculated from the first day of administering the agent.

15. A method of treating borderline resectable or locally advanced pancreatic adenocarcinoma in a subject, comprising:
    administering to the subject about 750 mg of durvalumab about every 14 days or about every 28 days; and
    administering to the subject radiotherapy comprising (1) image guided radiotherapy (IGRT), (2) intensity modulated radiation therapy (IMRT), (3) volumetric modulated arc therapy (VMAT), and (4) stereotactic body radiation therapy (SBRT), wherein the SBRT is administered starting on about day 8, calculated from the first day of administering durvalumab, at about 6.6 Gy per fraction about every other day for 5 fractions,
    thereby treating the borderline resectable or locally advanced pancreatic adenocarcinoma in the subject.

16. The method of claim 15, wherein the durvalumab is administered until surgical resection.

17. The method of claim 1, wherein the durvalumab is administered in the amount of about 100 mg-500 mg.

18. The method of claim 1, wherein the durvalumab is administered in the amount of about 500 mg-1000 mg.

19. The method of claim 1, wherein the durvalumab is administered in the amount of about 600 mg-800 mg.

20. The method of claim 1, wherein the SBRT is used in conjunction with image guided radiotherapy (IGRT).

21. The method of claim 1, wherein the SBRT is used in conjunction with intensity modulated radiation therapy (IMRT).

22. The method of claim 1, wherein the SBRT is used in conjunction with volumetric modulated arc therapy (VMAT).

* * * * *